US011154269B2

(12) United States Patent
Shea et al.

(10) Patent No.: US 11,154,269 B2
(45) Date of Patent: Oct. 26, 2021

(54) MULTIMODAL RADIATION APPARATUS AND METHODS

(71) Applicant: Accuray, Inc., Sunnyvale, CA (US)

(72) Inventors: Jacob Shea, Madison, WI (US); Brandon Frederick, Raleigh, NC (US); Eric Schnarr, McFarland, WI (US); Daniel Gagnon, Twinsburg, OH (US)

(73) Assignee: Accuray Inc., Sunnyvale, CA (US)

( * ) Notice: Subject to any disclaimer, the term of this patent is extended or adjusted under 35 U.S.C. 154(b) by 0 days.

(21) Appl. No.: 16/694,145

(22) Filed: Nov. 25, 2019

(65) Prior Publication Data
US 2020/0170598 A1 Jun. 4, 2020

Related U.S. Application Data

(60) Provisional application No. 62/773,712, filed on Nov. 30, 2018, provisional application No. 62/773,700,
(Continued)

(51) Int. Cl.
*A61B 6/00* (2006.01)
*A61B 6/03* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01);
(Continued)

(58) Field of Classification Search
CPC .... A61N 5/1067; A61N 5/107; A61N 5/1071; A61N 5/1082; A61N 2005/1085;
(Continued)

(56) References Cited

U.S. PATENT DOCUMENTS 4,190,773 A 2/1980 Braden
5,615,279 A 3/1997 Yoshioka et al.
(Continued)

FOREIGN PATENT DOCUMENTS

DE 10 2006 007058 A1 7/2007
EP 1062914 A1 12/2000
(Continued)

OTHER PUBLICATIONS

International Search Report and Written Opinion from PCT/US2019/063080 dated Mar. 16, 2020.
(Continued)

*Primary Examiner* — Courtney D Thomas
(74) *Attorney, Agent, or Firm* — Calfee, Halter & Griswold LLP

(57) ABSTRACT

Multimodal imaging apparatus and methods include a rotatable gantry system with multiple sources of radiation comprising different energy levels (for example, kV and MV). Fast slip-ring technology and helical scans allow data from multiple sources of radiation to be combined or utilized to generate improved images and workflows, including for IGRT. Features include increasing the precision of spatial registrations between respective image sets to allow more precise radiation treatment delivery, reducing image artifacts (e.g., scatter, metal and beam hardening, image blur, motion, etc.), and utilization of dual energy imaging (e.g., for material separation and quantitative imaging, patient setup, online adaptive IGRT, etc.).

24 Claims, 14 Drawing Sheets

Related U.S. Application Data filed on Nov. 30, 2018, provisional application No. 62/796,831, filed on Jan. 25, 2019, provisional application No. 62/800,287, filed on Feb. 1, 2019, provisional application No. 62/801,260, filed on Feb. 5, 2019, provisional application No. 62/813,335, filed on Mar. 4, 2019, provisional application No. 62/821,116, filed on Mar. 20, 2019, provisional application No. 62/836,357, filed on Apr. 19, 2019, provisional application No. 62/836,352, filed on Apr. 19, 2019, provisional application No. 62/843,796, filed on May 6, 2019, provisional application No. 62/878,364, filed on Jul. 25, 2019.

(51) Int. Cl.

| | | |
|---|---|---|
| *A61B 6/02* | (2006.01) | |
| *G06T 11/00* | (2006.01) | |
| *A61B 6/06* | (2006.01) | |
| *A61N 5/10* | (2006.01) | |
| *A61B 6/08* | (2006.01) | |
| *G06T 7/30* | (2017.01) | |
| *A61B 5/055* | (2006.01) | |
| *A61B 6/04* | (2006.01) | |

(52) U.S. Cl.
CPC ............ *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01); *A61B 6/035* (2013.01); *A61B 6/0407* (2013.01); *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1049* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(58) Field of Classification Search
CPC .... A61N 2005/1091; A61N 2005/1095; A61N 5/1081; A61N 5/1049; A61N 5/1042; A61N 2005/1061; A61B 6/4283; A61B 6/4028; A61B 6/541; A61B 6/4021; A61B 6/405; A61B 6/5205; A61B 6/025; A61B 6/027; A61B 6/4435; A61B 6/482; A61B 6/469; A61B 6/481; A61B 6/484; A61B 6/035; A61B 6/4014; A61B 6/5282; A61B 6/582; A61B 5/055; A61B 6/032; A61B 6/0407; A61B 6/06; A61B 6/4078; A61B 6/4085; A61B 6/4441; A61B 6/4458; A61B 6/485; A61B 6/488; A61B 6/08; A61B 6/4064; A61B 6/483; A61B 6/03; A61B 8/488; A61B 6/545; A61B 6/542; A61B 6/0487; A61B 6/4258; A61B 6/5235; A61B 6/5264; A61B 6/4233; A61B 6/5258; A61B 6/50; G06T 7/30; G06T 11/008; G06T 11/005; G06T 2211/404; G06T 2211/412; G06T 2207/10081; G06T 2210/41; G06T 2211/432; G06T 2211/424; G06T 2211/428

See application file for complete search history.

(56) References Cited

U.S. PATENT DOCUMENTS

| | | | |
|---|---|---|---|
| 6,233,478 | B1 | 5/2001 | Liu |
| 6,307,909 | B1 | 10/2001 | Flohr et al. |
| 7,050,528 | B2 | 5/2006 | Chen |
| 7,660,380 | B2 | 2/2010 | Boese et al. |
| 8,116,430 | B1 | 2/2012 | Shapiro et al. |
| 8,467,497 | B2 | 6/2013 | Lu et al. |
| 8,588,363 | B2 | 11/2013 | Flohr |
| 9,400,332 | B2 | 7/2016 | Star-Lack et al. |
| 2003/0076927 | A1 | 4/2003 | Shigeyuki et al. |
| 2004/0091079 | A1 | 5/2004 | Zapalac |
| 2004/0202360 | A1 | 10/2004 | Besson |
| 2005/0053188 | A1 | 3/2005 | Gohno |
| 2005/0251029 | A1 | 11/2005 | Khamene et al. |
| 2006/0109954 | A1 | 5/2006 | Gohno |
| 2006/0262894 | A1 | 11/2006 | Bernhadt et al. |
| 2007/0127621 | A1 | 6/2007 | Grass et al. |
| 2007/0189444 | A1 | 8/2007 | Van Steven-Daal et al. |
| 2008/0112532 | A1 | 5/2008 | Schlomka et al. |
| 2009/0080603 | A1 | 3/2009 | Shukla et al. |
| 2009/0135994 | A1 | 5/2009 | Yu et al. |
| 2009/0161826 | A1 | 6/2009 | Gertner et al. |
| 2009/0225932 | A1 | 9/2009 | Zhu et al. |
| 2009/0283682 | A1* | 11/2009 | Star-Lack ............ A61B 6/482 250/363.1 |
| 2010/0046819 | A1 | 2/2010 | Noo et al. |
| 2010/0208964 | A1 | 8/2010 | Wiegert et al. |
| 2011/0142312 | A1* | 6/2011 | Toth .................... G06T 11/005 382/131 |
| 2012/0014582 | A1 | 1/2012 | Schaefer et al. |
| 2012/0207370 | A1 | 8/2012 | Fahimian et al. |
| 2012/0263360 | A1 | 10/2012 | Zhu et al. |
| 2012/0294504 | A1 | 11/2012 | Kyriakou |
| 2013/0101082 | A1 | 4/2013 | Jordan et al. |
| 2013/0294570 | A1 | 11/2013 | Hansis |
| 2014/0018671 | A1 | 1/2014 | Li et al. |
| 2014/0086383 | A1 | 3/2014 | Huwer et al. |
| 2015/0297165 | A1 | 10/2015 | Tanaka et al. |
| 2015/0305696 | A1 | 10/2015 | Yamakawa et al. |
| 2016/0016009 | A1 | 1/2016 | Manzke et al. |
| 2016/0120486 | A1 | 5/2016 | Goto et al. |
| 2016/0262709 | A1 | 9/2016 | Siewerdsen et al. |
| 2017/0000428 | A1 | 1/2017 | Goto |
| 2017/0197098 | A1 | 7/2017 | Hirasawa et al. |
| 2017/0205360 | A1 | 7/2017 | Cinquin et al. |
| 2017/0332982 | A1 | 11/2017 | Koehler et al. |
| 2018/0070894 | A1 | 3/2018 | Osaki et al. |
| 2018/0192978 | A1 | 7/2018 | Naylor |
| 2018/0345042 | A1 | 12/2018 | Voronenko et al. |
| 2020/0121267 | A1 | 4/2020 | Deutschmann |
| 2021/0165122 | A1 | 6/2021 | Morton |

FOREIGN PATENT DOCUMENTS

| | | | |
|---|---|---|---|
| EP | 2383702 | A1 | 11/2011 |
| JP | H09 218939 | A | 8/1997 |
| JP | 2004 136021 | | 5/2004 |
| JP | 2008 036275 | | 2/2008 |
| WO | 2005/112753 | A2 | 12/2005 |
| WO | 2006/078386 | A2 | 7/2006 |
| WO | 2010/014288 | A1 | 2/2010 |
| WO | 2010/099621 | A1 | 9/2010 |
| WO | 2015/103184 | A1 | 7/2015 |

(56) References Cited

FOREIGN PATENT DOCUMENTS

| WO | 2018/156968 A1 | 8/2018 |
|---|---|---|
| WO | 2018/183748 A1 | 10/2018 |

OTHER PUBLICATIONS

International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063078 dated Oct. 8, 2020.
International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.
International Search Report and Written Opinion from PCT/US2019/063076 dated Mar. 16, 2020.
International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.
Spearman, et al. Effect of Automated Attenuation-Based Tube Voltage Selection on Radiation Dose at CT: An Observational Study on a Global Scale11 , RADIOLOGY, vol. 279, No. Apr. 1, 2016 (Apr. 1, 2016), pp. 167-174, XP055734550.
Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.
Wang et al., "A General Cone-Beam Reconstruction Algorithm," IEEE Transactions on Medical Imaging, vol. 12, No. 3, Sep. 1, 1993.
Wang, "X-Ray Micro-CT With a Displaced Detector Array," Medical Physics, vol. 29, No. 7, Jul. 1, 2002.
Restriction Requirement from U.S. Appl. No. 16/694,210 dated Jun. 10, 2021 (6 pages).
Office Action from U.S. Appl. No. 16/694,190 dated Mar. 26, 2021 (9 pages).
Notice of Allowance from U.S. Appl. No. 16/694,190 dated Jun. 23, 2021 (8 pages).
Office Action from U.S. Appl. No. 16/694,230 dated Apr. 1, 2021 (6 pages).
Office Action from U.S. Appl. No. 16/694,202 dated Apr. 9, 2021 (12 pages).
Office Action from U.S. Appl. No. 16/694,192 dated Jun. 10, 2021 (10 pages).
Office Action from U.S. Appl. No. 16/694,218 dated Apr. 15, 2021 (7 pages).
Clackdoyle, R. and Desbat, L., "Data consistency conditions for truncated fanbeam and parallel projections." Med. Phys. 42 (2015), pp. 831-845.
Defrise, M., Noo, F. and Kudo, H., "A solution to the long-object problem in helical cone-beam tomography." Phys. Vied. Biol. 45 (2000) pp. 623-643.
Noo et al., "A new scheme for view-dependent data differentiation in fan-beam and cone-beam computed tomography" Phys. Med. Biol. 52 (2007) pp. 5393-5414.
Hsieh, J., et al. "A novel reconstruction algorithm to extend the CT scan field-of-view." Med. Phys. 31(9), 2004, pp. 2385-2391.
Katsevich, A., "An improved exact filtered backprojection algorithm for spiral computed tomography." Advances in Applied Mathematics, 32(2004), pp. 681-697.
Kudo et al., "Exact and approximate algorithms for helical cone-beam CT", Phys. Med. Biol. 49(13), 2004, pp. 2913-2931.
Kunze, et al., "Cone beam reconstruction with displaced flat panel detector", 10th International Meeting on Fully Three-Dimensional Image Reconstruction in Radiology and Nuclear Medicine, 2009, pp. 138-141.
Li et al., "Scatter kernel estimation with an edge-spread function method for cone-beam computed tomography imaging," Phys. Med. Biol. 51 (2008) pp. 6729-6748.
Maslowski, et al. "Acuros CTS: A fast, linear Boltzmann transport equation solver for computed tomography scatter-Part I: Core algorithms and validation." Med. Phys. 45 (5), 2018, pp. 1899-1913.
Ming, et al., "X-ray scatter correction algorithm for cone beam CT imaging." Med. Phys. 31 (5), 2004, pp. 1195-1202.
Schafer, et al., "FBP and BPF reconstruction methods for circular X-ray tomography with off-center detector", Med. Phys., 38(7), 2011, pp. S85-S94.
Schafer, et al., "Cone-beam filtered back-projection for circular X-ray tomography with off-center detector", 10th International Meeting on Fully Three-Dimensional Image Reconstruction in Radiology and Nuclear Medicine, 2009, pp. 86-89.
Siewerdsen, et al., "A simple, direct method for x-ray scatter estimation and correction in digital radiography and conebeam CT." Med. Phys., 33(1), 2006, pp. 187-197.
Sun, et al. "Improved scatter correction using adaptive scatter kernel superposition." Phys. Med. Biol. 55(22), 2010, pp. 6695-6720.
Tang, et al., "A sinogram extrapolation method for CT field of view extension." Proceedings of the Fifth CT Meeting, 2018, pp. 206-209.
Yu, L., et al., "Radiation dose reduction in computed tomography: techniques and future perspective." Imaging Med. 1 (1), 2009, pp. 65-84.
Zamyatin et al., "Helical cone beam CT with an asymmetrical detector," Med. Phys. 32 (10), 2005, pp. 3117-3127.
Zbijewski, W. et al. "Efficient Monte Cado based scatter artifact reduction in cone-beam micro-CT." IEEE transactions an medical imaging, 25(7), 2006, pp. 817-827.
Zhu, et al. "Scatter correction method for X-ray CT using primary modulation: Theory and preliminary results." IEEE transactions on medical imaging, 25(12), 2006, pp. 1573-1587.
Office Action from U.S. Appl. No. 16/694,161 dated Sep. 13, 2021, 18 pages.

\* cited by examiner

MULTIMODAL RADIATION APPARATUS AND METHODS

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including Ser. No. 16/694,148, filed Nov. 25, 2019, entitled "APPARATUS AND METHODS FOR SCALABLE FIELD OF VIEW IMAGING USING A MULTI-SOURCE SYSTEM;" Ser. No. 16/694,161, filed Nov. 25, 2019, entitled "INTEGRATED HELICAL FAN-BEAM COMPUTED TOMOGRAPHY IN IMAGE-GUIDED RADIATION TREATMENT DEVICE;" Ser. No. 16/694,166, filed Nov. 25, 2019, entitled "COMPUTED TOMOGRAPHY SYSTEM AND METHOD FOR IMAGE IMPROVEMENT USING PRIOR IMAGE;" Ser. No. 16/694,177, filed Nov. 25, 2019, entitled "OPTIMIZED SCANNING METHODS AND TOMOGRAPHY SYSTEM USING REGION OF INTEREST DATA;" Ser. No. 16/694,190, filed Nov. 25, 2019, entitled "HELICAL CONE-BEAM COMPUTED TOMOGRAPHY IMAGING WITH AN OFF-CENTERED DETECTOR;" Ser. No. 16/694,192, filed Nov. 25, 2019, entitled "MULTI-PASS COMPUTED TOMOGRAPHY SCANS FOR IMPROVED WORKFLOW AND PERFORMANCE;" Ser. No. 16/694,202, filed Nov. 25, 2019, entitled "METHOD AND APPARATUS FOR SCATTER ESTIMATION IN CONE-BEAM COMPUTED TOMOGRAPHY;" Ser. No. 16/694,210, filed Nov. 25, 2019, entitled "ASYMMETRIC SCATTER FITTING FOR OPTIMAL PANEL READOUT IN CONE-BEAM COMPUTED TOMOGRAPHY;" Ser. No. 16/694,218, filed Nov. 25, 2019, entitled "METHOD AND APPARATUS FOR IMPROVING SCATTER ESTIMATION AND CORRECTION IN IMAGING;" and Ser. No. 16/694,230, filed Nov. 25, 2019, entitled "METHOD AND APPARATUS FOR IMAGE RECONSTRUCTION AND CORRECTION USING INTER-FRACTIONAL INFORMATION." The contents of all above-identified patent application(s) and patent(s) are fully incorporated herein by reference.

FIELD OF THE INVENTION

Aspects of the disclosed technology relate to utilizing multimodal radiation for imaging, and, more particularly, utilizing low-energy radiation (e.g., kilovolt (kV)) and high-energy radiation (e.g., megavolt (MV)) in combination for improved imaging, including for computed tomography (CT) scans.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy, which typically uses a therapeutic radiation source, such as a linear accelerator (LINAC), to generate radiation beams, such as x-rays. In one type of external beam radiation therapy, a therapeutic radiation source directs a sequence of x-ray beams at a tumor site from multiple angles, with the patient positioned in the field of view of the beam. As the angle of the therapeutic radiation source changes, every beam passes through the tumor site, but passes through a different area of healthy tissue on its way to and from the tumor. As a result, the cumulative radiation dose at the tumor is high and that to healthy tissue is relatively low.

The term "radiosurgery" refers to a procedure in which radiation is applied to a target region at doses sufficient to necrotize a pathology in fewer treatment sessions or fractions than with delivery of lower doses per fraction in a larger number of fractions. Radiosurgery is typically characterized, as distinguished from radiotherapy, by relatively high radiation doses per fraction (e.g., 500-2000 centigray) and hypo-fractionation (e.g., one to five fractions or treatment days). Radiotherapy is typically characterized by a low dose per fraction (e.g., 100-200 centigray) and hyper-fractionation (e.g., 30 to 45 fractions). For convenience, the terms "radiation treatment" and "radiation therapy" are used interchangeably herein to mean radiosurgery and/or radiotherapy unless otherwise noted.

Image-guided radiation therapy (IGRT) systems include gantry-based systems and robotic arm-based systems. In gantry-based systems, a gantry rotates the therapeutic radiation source around an axis passing through the isocenter. Gantry-based systems include C-arm gantries, in which the therapeutic radiation source is mounted, in a cantilever-like manner, over and rotates about the axis passing through the isocenter. Gantry-based systems further include ring gantries having generally toroidal shapes in which the patient's body extends through a bore of the ring/toroid, and the therapeutic radiation source is mounted on the perimeter of the ring and rotates about the axis passing through the isocenter. Traditional gantry systems (ring or C-arm) deliver therapeutic radiation with a set angle defined by the rotational trajectory of the radiation source. In robotic arm-based systems, the therapeutic radiation source is mounted on an articulated robotic arm that extends over and around the patient, the robotic arm being configured to provide at least five degrees of freedom. Robotic arm-based systems provide the capability to deliver therapeutic radiation from multiple out-of-plane directions, i.e., are capable of non-coplanar delivery.

Associated with each radiation therapy system is an imaging system to provide in-treatment images that are used to set up and, in some examples, guide the radiation delivery procedure and track in-treatment target motion. MV imaging systems can place a detector opposite the therapeutic source to image the patient for setup and in-treatment images, while other approaches utilize distinct, independent image radiation source(s) and/or detector(s) for the patient set-up and in-treatment images. Target or target volume tracking during treatment is accomplished by comparing in-treatment images to prior or pre-treatment image information. Pre-treatment image information may comprise, for example, CT data, cone-beam CT (CBCT) data, magnetic resonance imaging (MRI) data, positron emission tomography (PET) data or 3D rotational angiography (3DRA) data, and any information obtained from these imaging modalities (for example and without limitation, digitally reconstructed radiographs (DRRs)).

In one common scenario, the therapeutic source is a LINAC producing therapeutic radiation (which can be, e.g., a MV source) and the imaging system comprises one or more independent x-ray imaging sources producing lower energy imaging radiation (each of which can be, e.g., a kV source). In-treatment images can comprise one or more (preferably at least two) two-dimensional images (typically x-ray) acquired at one or more different points of view (e.g., stereoscopic x-ray images), and can be compared, for example, to two-dimensional DRRs derived from the three dimensional pre-treatment image information. A DRR is a synthetic x-ray image generated by casting hypothetical x-rays through the 3D imaging data, where the direction and orientation of the hypothetical x-rays simulate the geometry of the in-treatment x-ray imaging system. The resulting DRR then has approximately the same scale and point of view as the in-treatment x-ray imaging system and can be compared with the in-treatment x-ray images to determine the position and orientation of the target, which can then be used to guide delivery of radiation to the target.

In another common scenario, either the therapeutic radiation source or an independent x-ray imaging source (e.g., a kV source) mounted on the gantry is used to acquire multiple views and reconstruct a volumetric image—a CT image. Views—also called projections—are acquired for at least 180 degrees plus the imaging beam fan angle to provide full mathematical support for reconstructing a 3-D volume or individual axial slices. The imaging detector mounted opposite the x-ray source can be a single row detector used to acquire data for a single slice at a time, or a multi-row detector or fully 2-D flat panel detector to acquire data for many slices at once.

There are typically two general goals in radiation therapy: (i) to deliver a highly conformal dose distribution to the target volume (by utilizing CT imaging to conform the delivery/dose of radiation to the shape of the target; normal tissue is spared as much as possible); and (ii) to deliver treatment beams with high accuracy throughout every treatment fraction. A third goal is to accomplish the two general goals in as little time per fraction as possible. Delivering a more conformal dose distribution may require, for example, the ability to deliver non-coplanar beams. Delivering treatment beams accurately may require the ability to track the location of the target volume intrafraction. The ability to increase delivery speed requires the ability to accurately, precisely, and quickly move the radiation source without hitting other objects in the room or the patient, and/or violating regulatory agency speed limitations.

Ring gantry-based systems exhibit relatively high mechanical stability and can reproducibly and accurately position the radiation source, including doing so at relatively high mechanical drive speeds, thereby avoiding some of the limitations exhibited by robotic and/or C-arm gantry-based systems.

Regarding in-treatment imaging, X-ray tomosynthesis has been proposed as an in-treatment kV imaging modality for use in conjunction with radiation treatment systems. X-ray tomosynthesis refers to the process of acquiring a number of two-dimensional x-ray projection images of a target volume using x-rays that are incident upon the target volume at a respective number of different angles, followed by the mathematical processing of the two-dimensional x-ray projection images to yield a set of one or more tomosynthesis reconstructed images representative of one or more respective slices of the target volume, wherein the number of x-ray projection images is less than that in a set that would be required for CT image reconstruction, and/or the number or range of incident radiation angles is less than would be used in a CT imaging procedure. Commonly, a plurality of tomosynthesis reconstructed images are generated, each being representative of a different slice of the target volume, and therefore a set of tomosynthesis reconstructed images is sometimes referred to as a tomosynthesis volume. As used herein, the term tomosynthesis projection image refers to one of the two-dimensional x-ray projection images acquired during the tomosynthesis imaging process.

For purposes of the above terminology, for some preferred embodiments, a set of images that is required for CT image reconstruction is considered to include images (e.g., 300 or more) generated over a range of source angles that is at least 180 degrees plus the fan beam angle. For some preferred embodiments, the x-ray projection images for constructing a tomosynthesis image are taken over an angular range between 1 degree and an angular range value that is less than that needed for a complete projection set for CT imaging (e.g., 180 degrees plus the fan angle), wherein the number of projection images generated in this range is a value that is between 2 and 1000. In other preferred embodiments, the x-ray projection images for constructing a tomosynthesis image are taken over an angular range of between 5 degrees and 45 degrees, wherein the number of projection images generated in this range is between 5 and 100.

U.S. Pat. No. 6,778,850, which is incorporated by reference herein, discloses the use of x-ray tomosynthesis images (more particularly, the use of relatively low clarity intra-treatment 3D images of the target region synthesized from a plurality of 2D diagnostic images acquired at different angles) as an in-treatment kV imaging modality.

CBCT has also been proposed as an in-treatment imaging modality for use in conjunction with radiation treatment systems, in some cases as a kV imaging modality and in other cases as a MV (portal) imaging modality. Whereas conventional CT imaging reconstructs 2D slices from 1D projections through a target volume, the 2D slices then being stacked to form a 3D volumetric image, CBCT imaging directly constructs a 3D volumetric image from 2D projections of the target volume. CBCT offers the ability to form a 3D image volume from a single gantry rotation (more specifically, a rotation of at least 180 degrees plus a fan beam angle) about the target volume, whereas conventional CT requires more rotations to form the same image volume, including, for example, one rotation per slice (for single-row detectors) or 1/M rotations per slice (for quasi-linear multi-row detectors having M rows). CBCT also provides for a more isotropic spatial resolution, whereas conventional CT limits the spatial resolution in the longitudinal direction to the slice thickness. However, because conventional CT systems usually offer a substantially higher degree of collimation near their linear or quasi-linear row detectors than can usually be afforded by CBCT systems near their two-dimensional detectors, scattering noise and artifacts are more of a problem for CBCT systems than for conventional CT systems. In addition, a major issue with single rotation CBCT (other than scatter) is insufficient sampling on all slices except for the central slice (the one containing the rotation).

Prior to treatment, a planning image can be acquired for treatment planning. Subsequently, before each treatment fraction, a CBCT image can be acquired and compared to the pre-treatment planning image, and the results of the comparison used to modify the treatment plan for that treatment fraction, for example, to compensate for inter-fraction setup errors and/or inter-fraction organ motion. Due to limitations in permissible C-arm gantry rotation speeds (e.g., one rotation per minute) which cause the CBCT acquisition time to be slow compared to breathing (or other physiological cycles) of the patient, a gating scheme synchronized to patient breathing (or other physiological cycles) can be used during CBCT acquisition to reduce the deleterious effects of organ motion in the reconstructed images. Also, due to the relatively slow CBCT acquisition time, the CBCT volume data is generally useful only for patient set-up before each treatment fraction, and not for intra-fraction motion correction.

U.S. Pat. No. 9,687,200, which is incorporated by reference herein, discloses the use of a translatable ring gantry for radiation treatment. An IGRT apparatus is provided comprising a ring gantry having a central opening and a radiation treatment head coupled to the ring gantry that is rotatable around the central opening in at least a 180 degree arc.

One or more issues arise with respect to known medical imaging and/or radiation treatment systems that are at least partially addressed by one or more of the embodiments described further herein below. For example, increasing the precision of spatial registrations between respective image sets to allow more precise radiation treatment delivery, reducing image artifacts (e.g., scatter, metal and beam hardening, image blur, motion, etc.), and utilization of dual energy imaging (e.g., for material separation and quantitative imaging, patient setup, online adaptive IGRT, etc.).

BRIEF SUMMARY

In one embodiment, a multimodal imaging apparatus includes a rotatable gantry system positioned at least partially around a patient support, a first source of radiation coupled to the rotatable gantry system, the first source of radiation configured for imaging radiation, a second source of radiation coupled to the rotatable gantry system, the second source of radiation configured for at least one of imaging radiation or therapeutic radiation, wherein the second source of radiation has an energy level more than the first source of radiation, and a first radiation detector coupled to the rotatable gantry system and positioned to receive radiation from at least one of the first source of radiation or the second source of radiation, wherein a first measured projection data from the first source of radiation comprises more attenuation than a second measured projection data from the second source of radiation, and wherein a first attenuation estimate associated with the first measured projection data is based on the second measured projection data.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
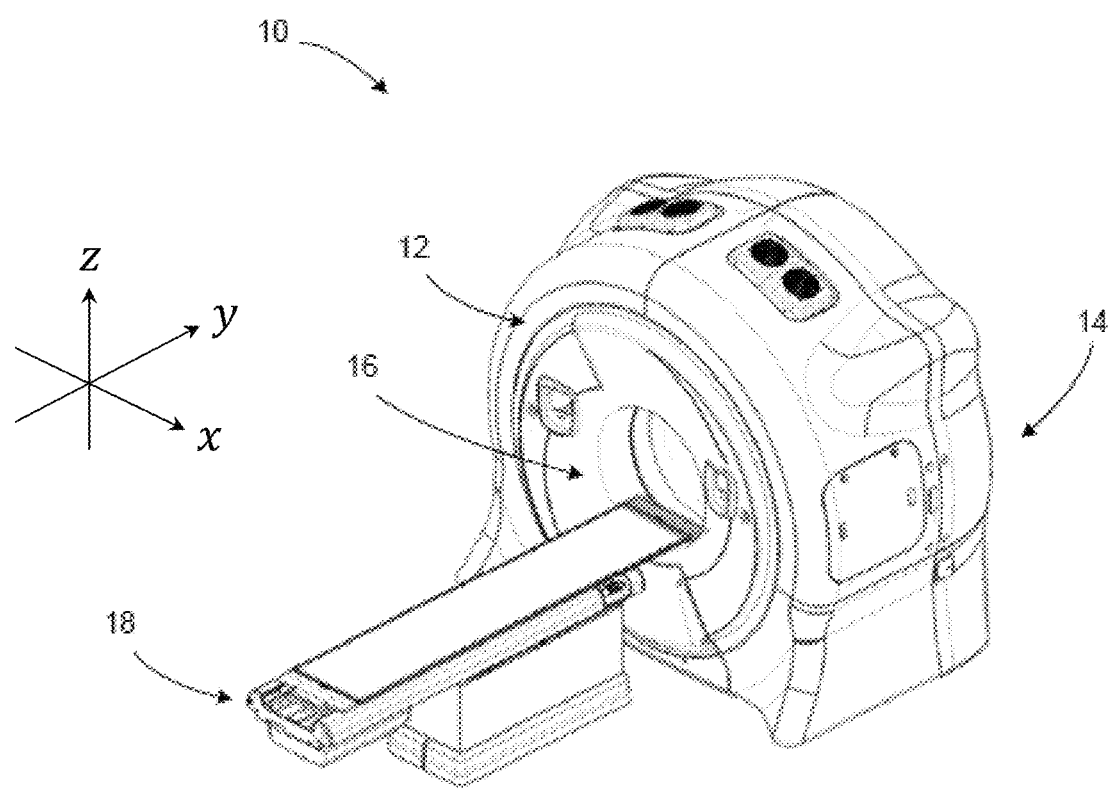
FIG. 1 is a perspective view of an exemplary multimodal radiotherapy apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to multimodal imaging/radiotherapy devices and methods. In some embodiments, a radiotherapy delivery device and method can make use of an integrated low-energy radiation source for imaging and a high-energy radiation source for treatment and/or imaging in conjunction with or as part of IGRT. In particular, for example, a radiotherapy delivery device and method can combine a low-energy collimated radiation source for imaging in a gantry using rotational (e.g., helical or step-and-shoot) image acquisition along with a high-energy radiation source for imaging and/or therapeutic treatment. Complementary information and advantages can be exploited from a low-energy radiation source (e.g., kV) and from a high-energy radiation source (e.g., MV). For example, the intrinsic contrast of soft tissues may be higher at low-energies, while there is no starvation of primary photons through wide or dense structures at high-energies. KV and MV imaging data can be used to supplement each other to yield higher quality images. High quality volume imaging can be needed for visualization of targets and organs-at-risk (OARS), for adaptive therapy monitoring, and for treatment planning/re-planning. In some embodiments, the multimodal system can also be used for positioning, motion tracking, and/or characterization or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc.

In accordance with various embodiments, the multimodal apparatus collimates a radiation source, including, for example, into a cone beam or a fan beam using, for example, a beamformer (which may include a collimator) to limit the beam. In one embodiment, the collimated beam can be combined with a gantry that continuously rotates while the patient moves, resulting in a helical image acquisition.

In some embodiments, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high frame rates, and/or sparse data reconstruction techniques, to provide CT quality imaging on a radiation therapy delivery platform. Detectors (with various row/slice sizes, configurations, dynamic range, etc.), scan pitch, and/or dynamic collimation are additional features in various embodiments, including to selectively expose portions of the detector and selectively define active readout areas.

The multimodal apparatus and methods can provide selective and variable collimation of a radiation beam emitted by the source of radiation, including adjusting the radiation beam shape to expose less than the entire active area of an associated radiation detector (e.g., a radiation detector positioned to receive radiation from the x-ray radiation source). Also, exposing only a primary region of the detector to direct radiation allows shadowed regions of the detector to receive only scatter. In some embodiments, scatter measurements in the shadow region (and in some embodiments measurements in the penumbra region) of the detector can be used to estimate scatter in the primary region of the detector receiving projection data.

The multimodal apparatus and method can provide selective and variable detector readout areas and ranges, including adjusting the detector readout range to limit the active area of the detector for improved readout speed. For example, less than the available shadow region data may be read and used for scatter estimation. Combining selective readout with beamforming allows for various optimizations of scatter fitting techniques.

Figure 2:
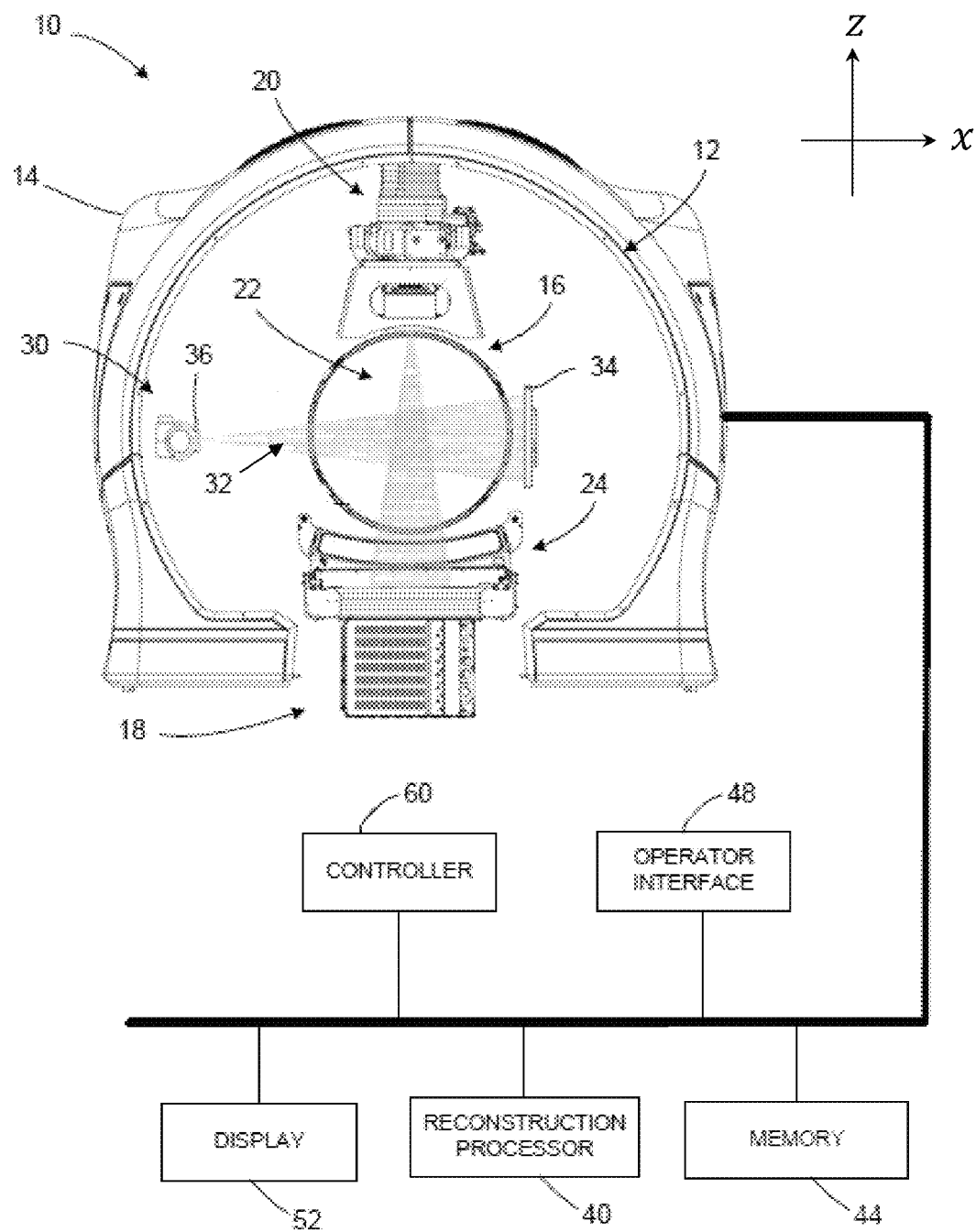
FIG. 2 is a diagrammatic illustration of an exemplary multimodal radiotherapy device in accordance with one aspect of the disclosed technology.

With reference to FIG. 1 and FIG. 2, a multimodal apparatus 10 is shown. It will be appreciated that the multimodal apparatus 10 may be associated with and/or integrated into a radiotherapy device (as shown in FIG. 2) that can be used for a variety of applications, including, but not limited to IGRT, for example, as an IGRT delivery system (e.g., IGRT delivery system 104 shown in FIG. 3 and discussed in detail below). The multimodal apparatus 10 includes a rotatable gantry system, referred to as gantry 12, supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of radiation sources and associated radiation detector(s) while providing sufficient bandwidth for the high-quality imaging data received by the detector(s). A slip-ring gantry can eliminate gantry rotations in alternating directions in order to wind and unwind cables carrying the power and signals associated with the device. Such a configuration will allow for continuous helical computed tomography, including CBCT, even when integrated into an IGRT system. As mentioned above, a major issue with single rotation CBCT is insufficient sampling on all slices except for the central slice (the one containing the rotation). This can be overcome by helical trajectory cone-beam imaging.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. The patient support can also be moved in a limited range up and down, left and right once it is in the bore 16 to adjust the patient position for optimal treatment. Axes x, y, and z are shown, where, viewing from the front of the gantry 12, the x-axis is horizontal and points to the right, the y-axis points into the gantry plane, and the z-axis is vertical and points to the top. The x-, y-, and z-axes follow the right-hand rule.

As shown in FIG. 2, the multimodal apparatus 10 includes a low-energy radiation source (e.g., kV) 30 coupled to or otherwise supported by the rotatable gantry 12. In this embodiment, the low-energy radiation source 30 is a source of imaging radiation and emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). In one embodiment, the low energy radiation source comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments. An x-ray detector 34 (e.g., two-dimensional flat detector or curved detector) can be coupled to or otherwise supported by the rotatable gantry 12. The x-ray detector 34 is positioned to receive radiation from the x-ray source 30 and can rotate along with the x-ray source 30.

It will be appreciated that the x-ray detector 34 can take on a number of configurations without departing from the scope of the disclosed technology. As illustrated in FIG. 2, the x-ray detector 34 can be configured as a flat-panel detector (e.g., a multi-row flat panel detector). In accordance with another exemplary embodiment, the x-ray detector 34 can be configured as a curved detector. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the low-energy radiation source 30 rotates around and emits radiation toward the patient.

Although FIGS. 1 and 2 depict a multimodal apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A collimator or beamformer assembly (indicated generally as 36) is positioned relative to the x-ray source 30 to selectively control and adjust a shape of a radiation beam 32 emitted by the x-ray source 30 to selectively expose a portion or region of the active area of the x-ray detector 34. The beamformer can also control how the radiation beam 32 is positioned on the x-ray detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and/or translated.

The beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which may be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each readout, with about 1-2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector (e.g., beam size, beam/aperture center, collimation, pitch, detector readout range, detector readout center, etc.) such that the measured data is sufficient for primary (exposed) and shadowed regions, but also optimized for speed and dosage control. The beamformer 36 shape/position and detector 34 readout range can be controlled such that the radiation beam 32 from the x-ray source 30 covers as much or as little of the x-ray detector 34 based on the particular imaging task and scatter estimation process being carried out, including, for example, combinations of narrow and wide axial field-of-view (aFOV) scans. The apparatus 10 has the ability to acquire both single rotation cone beam and wide and narrow beam angle images, helical or other.

The beamformer 36 may be configured in a variety of ways that allow it to adjust the shape of the radiation beam 32 emitted by the x-ray source 30. For example, the beamformer 36 can be configured to include a set of jaws or other suitable members that define and selectively adjust the size of an aperture through which the radiation beam from the x-ray source 30 may pass in a collimated manner. In accordance with one exemplary configuration, the beamformer 36 can include an upper jaw and a lower jaw, where the upper and lower jaws are movable in different directions (e.g., parallel directions) to adjust the size of the aperture through which the radiation beam from the x-ray source 30 passes, and also to adjust the beam 32 position relative to the patient to illuminate only the portion of the patient to be imaged for optimized imaging and minimized patient dose.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

As shown in FIG. 2, the multimodal apparatus 10 may be integrated with a radiotherapy device that includes a high-energy radiation source (e.g., MV) 20 coupled to or otherwise supported by the rotatable gantry 12. In accordance with one embodiment, the high-energy radiation source 20 is configured as a source of therapeutic radiation, such as a high-energy source of radiation used for treatment of a tumor within a patient in a region of interest. In other embodiments, the high-energy radiation source 20 is also configured as a source of imaging radiation, or at least utilized as such. It will be appreciated that the source of therapeutic radiation can be a high-energy x-ray beam (e.g., MV x-ray beam), and/or a high-energy particle beam (e.g., a beam of electrons, a beam of protons, or a beam of heavier ions, such as carbon) or another suitable form of high-energy radiation. In one embodiment, the high-energy radiation source 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the high-energy radiation source 20 has a higher energy level (peak and/or average, etc.) than the low-energy radiation source 30.

In one embodiment, the high-energy radiation source 20 is a LINAC producing therapeutic radiation (e.g., MV) and the imaging system comprises an independent low-energy radiation source 30 producing relatively low intensity and lower energy imaging radiation (e.g., kV). In other embodiments, the therapeutic radiation source 20 could be a radioisotope, such as, for example, Co-60, which can generally have energy >1 MeV. The high-energy radiation source 20 can emit one or more beams of radiation (indicated generally by 22) toward a region-of-interest (ROI) within a patient supported on the patient support 18 in accordance with a treatment plan.

In various embodiments, the high-energy radiation source 20 is utilized as a source of therapeutic radiation and a source of imaging radiation. As discussed in detail below, sources of radiation 20, 30 may be used in conjunction with one another to provide higher quality and better utilized images. References to the therapeutic radiation source 20 herein are to distinguish the high-energy radiation source 20 from the low-energy radiation source 30, which may be used only for imaging. However, references to the therapeutic radiation source 20 include embodiments where the therapeutic radiation source 20 (high-energy radiation source) can be utilized for therapy and/or imaging. In other embodiments, at least one additional radiation source can be coupled to the rotatable gantry 12 and operated to acquire projection data at a peak photon energy distinct from the peak photon energies of sources of radiation 20, 30.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a beamformer or collimator. The beamformer associated with the therapeutic radiation source 20 can be configured in a number of ways, similar to the beamformer 36 associated with the imaging source 30. For example, a beamformer can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

The therapeutic radiation source 20 may be mounted, configured, and/or moved into the same plane or a different plane (offset) than the imaging source 30. In some embodiments, scatter caused by simultaneous activation of the radiation sources 20, 30 may be reduced by offsetting the radiation planes.

In other embodiments, scatter can be avoided by interleaving the activations. For example, with simultaneous multimodal imaging, the acquisitions can be concurrent, without having concurrent individual pulses. In another embodiment, use of shadow-based scatter correction can be used, for example, to address the problem of MV scatter on a kV detector.

When integrated with a radiotherapy device, multimodal apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, CT data, cone-beam CT data, MRI data, PET data or 3D rotational angiography (3DRA) data, and/or any information obtained from these or other imaging modalities. In some embodiments, the multimodal apparatus 10 can track in-treatment patient, target, or ROI motion.

A reconstruction processor 40 can be operatively coupled to detector 24 and/or detector 34. In one embodiment, the reconstruction processor 40 is configured to generate patient images based on radiation received by the detectors 24, 34 from the radiation sources 20, 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The multimodal apparatus 10 can include an operator/user interface 48, where an operator of the apparatus 10 can interact with or otherwise control the apparatus 10 to provide input relating to scan or imaging parameters and the like. The operator interface 48 can include any suitable input devices, such as a keyboard, mouse, voice-activated controller, or the like. The apparatus 10 can also include a display 52 or other human-readable element to provide output to the operator of the apparatus 10. For example, the display 52 can allow the operator to observe reconstructed patient images and other information, such as imaging or scan parameters, related to operation of the apparatus 10.

As shown in FIG. 2, the multimodal apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer controller, a controller coupled to the detector 24 and/or the x-ray detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, a multimodal apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with the apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with apparatus 10.

Multimodal apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented. For example, in various embodiments, the radiation sources 20, 30 can be operated such that the measured projection data from the radiation sources 20, 30 are acquired simultaneously (or essentially/nearly (quasi-) simultaneous, e.g., within about 50 ms of each other) or sequentially (e.g., separated by seconds, minutes, etc.)

It will be appreciated that radiation sources 20, 30 and detector(s) 24, 34 can be configured to provide rotation around the patient during an imaging and/or treatment scan in a number of ways. In one embodiment, synchronizing the motion and exposure of the source 20, 30 with the longitudinal motion of the patient support 18 can provide a continuous helical acquisition or scan of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The multimodal apparatus 10 is capable of volume-based and planar-based imaging acquisitions. For example, in various embodiments, the multimodal apparatus 10 may be used to acquire volume images and/or planar images and execute the associated processing, including scatter estimation/correction methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of apparatus 10 described above.

In one embodiment, the gantry 12 rotation speed, the patient support 18 speed, the beamformer shape, and/or the detector readout could all be constant during image acquisition. In other embodiments, one or more of these variables could change dynamically during image acquisition and/or treatment.

In other embodiments, these features can be combined with one or more other image-based activities or procedures, including, for example, patient set up, adaptive therapy monitoring, treatment planning, etc.

Figure 3:
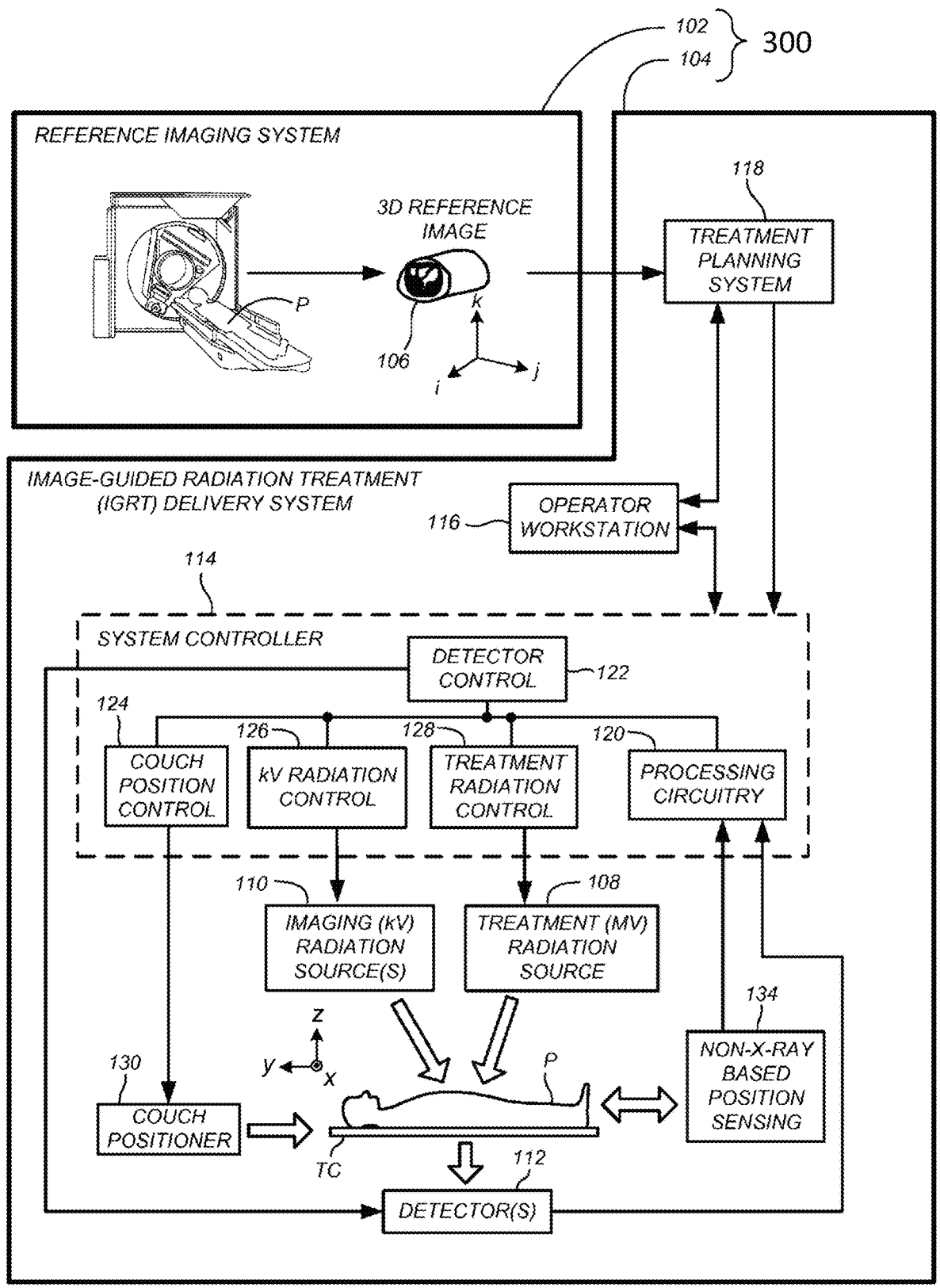
FIG. 3 illustrates an exemplary radiation treatment environment.

FIG. 3 illustrates an exemplary radiation treatment environment 300. The radiation treatment environment 300 includes a reference imaging system 102 and an IGRT system 104. The IGRT system 104 may comprise, for example, the multimodal apparatus 10 and its various components and devices as described above.

In one embodiment, the reference imaging system 102 can include a high precision volumetric imaging system such as, for example, a CT system or a MRI system. In view of cost and workflow considerations in many clinical environments, the reference imaging system 102 is often a general purpose tool used for a variety of different purposes in the clinic or hospital environment, and is not specifically dedicated to the IGRT system 104 or environment 300. Rather, the reference imaging system 102 may be located in its own separate room or vault and is purchased, installed, and/or maintained on a separate and more generalized basis than the IGRT system 104. Accordingly, for the embodiment of FIG. 3, the reference imaging system 102 is illustrated as being distinct from the IGRT system 104. In other embodiments, the reference imaging system 102 may be considered an integral component of the IGRT system 104. For example, the multimodal apparatus 10 has the capability to act as the reference imaging system 102 and the IGRT system 104.

In this embodiment, IGRT system 104 comprises a high-energy radiation treatment (MV) source 108 that selectively applies high-energy x-ray treatment radiation to a target volume of a patient P positioned on a patient support or treatment couch TC. The MV source 108 applies the treatment radiation under the control of system controller 114, and in one embodiment, more particularly a treatment radiation control subsystem 128. System controller 114 further comprises processing circuitry 120, a detector controller 122, a couch position controller 124, and a kV radiation controller 126, each programmed and configured to achieve one or more of the functionalities described further herein. One or more imaging (kV) radiation sources 110 selectively emit relatively low-energy x-ray imaging radiation under the control of kV radiation controller 126, the imaging radiation being captured by one or more detectors 112. One or more of the detectors 112 can capture high-energy x-ray treatment radiation from MV source 108 that has propagated through the target volume.

Each kV radiation source 110 and the MV radiation source 108 have a precisely measurable and/or precisely determinable geometry relative to the (x, y, z) coordinate system of the IGRT system 104 and/or treatment room since they are dynamically moveable.

A couch positioner 130 can be actuated by the couch position controller 124 to position the couch TC. In some embodiments, a non-x-ray based position sensing system 134 senses position and/or movement of external marker(s) strategically affixed to the patient, and/or senses position and/or movement of the patient skin surface itself, using one or more methods that do not involve ionizing radiation, such as optically based or ultrasonically based methods. IGRT system 104 further includes an operator workstation 116 and a treatment planning system 118.

In common clinical practice, treatment planning is performed on a pre-acquired treatment planning image or prior image data 106 generated by the reference imaging system 102. The pre-acquired treatment planning image 106 is often a high resolution three-dimensional CT image acquired substantially in advance (e.g., one to two days in advance) of the one or more radiation treatment fractions that the patient will undergo. As indicated in FIG. 3 by the illustration of an (i, j, k) coordinate system for the pre-acquired treatment planning image 106, which is in contrast to the (x, y, z) treatment room coordinate system illustrated for the treatment room of the IGRT system 104, there is generally no pre-existing or intrinsic alignment or registration between the treatment planning image 106 coordinate system and the treatment room coordinate system. During the treatment planning process, a physician typically establishes a coordinate system (e.g., i, j, k in treatment planning image 106) within the treatment planning image, which may also be referred to herein as the planning image coordinate system or planning image reference frame. A radiation treatment plan is developed in the planning image coordinate system that dictates the various orientations, sizes, durations, etc., of the high-energy treatment radiation beams to be applied by the MV source 108 during each treatment fraction. Accurate delivery of therapeutic radiation to a target requires aligning the planning image coordinate system with the treatment room coordinate system, as the entire delivery and tracking system (if present) is calibrated to the treatment room coordinate system. It will be appreciated that this alignment does not need to be exact and further appreciated that couch adjustment or beam delivery adjustment can be used to account for offsets in the alignment between the two coordinate systems.

In one embodiment, immediately prior to each treatment fraction, under image guidance via the kV imaging radiation source(s) 110, including according to one or more of the embodiments described further herein below, image-based pre-delivery steps may be performed. For example, the patient can be physically positioned or aligned such that the planning image coordinate system (defined, for example and not by way of limitation, by a physician while creating a treatment plan on a CT image or planning image) is positioned into an initial alignment with the treatment room coordinate system, hereinafter termed an initial treatment alignment or initial treatment position. This alignment is commonly referred to as patient set up or patient alignment. Depending on the location of the target volume, the target volume can vary in position and orientation and/or can undergo volumetric deformations due to patient movement and/or physiological cycles such as respiration. As used herein, the term in-treatment alignment variation or in-treatment position variation is used to refer to the variations in position, orientation, and/or volumetric shape by which the current state of the target volume differs from the initial treatment alignment. By virtue of a known relationship between the treatment planning coordinate system and the treatment room coordinate system, the term in-treatment alignment variation can also be used to refer to the variations in position, orientation, or volumetric shape by which the current state of the target volume differs from that in the treatment planning coordinate system. More generally, the term initial treatment alignment or initial treatment position refers herein to the particular physical pose or disposition (including position, orientation and volumetric shape) of the body part of the patient upon patient setup at the outset of the treatment fraction.

A non x-ray based position sensing system 134 may also be provided. This non x-ray based position sensing system 134 may include, for example, external markers affixed in some manner to a patient's chest which move in response to respiration, which can precisely determine target location. Other mechanisms for monitoring respiration may also be used. Other non-respiratory position sensing systems 134 may also be used, including, for example, quasi static positioning, EKG for cardiac gating, etc. System 134 can correlate motion of the external markers with target motion, as determined from, for example, mono or stereoscopic x-ray projections. Non x-ray based position sensing system 134, therefore, can permit system controller 114 to monitor external marker motion, use the correlation model to precisely predict where the target will be located in real time (e.g., ~60 Hz), and direct the treatment beam to the target. As treatment of the moving target progresses, additional x-ray images may be obtained and used to verify and update the correlation model.

As used herein, "registration" of medical images refers to the determination of a mathematical relationship between corresponding anatomical or other (e.g. fiducial) features appearing in those medical images. Registration can include, but is not limited to, the determination of one or more spatial transformations that, when applied to one or both of the medical images, would cause an overlay of the corresponding anatomical features. The spatial transformations can include rigid-body transformations and/or deformable transformations and can, if the medical images are from different coordinate systems or reference frames, account for differences in those coordinate systems or reference frames. For cases in which the medical images are not acquired using the same imaging system and are not acquired at the same time, the registration process can include, but is not limited to, the determination of a first transformation that accounts for differences between the imaging modalities, imaging geometries, and/or frames of reference of the different imaging systems, together with the determination of a second transformation that accounts for underlying anatomical differences in the body part that may have taken place (e.g., positioning differences, overall movement, relative movement between different structures within the body part, overall deformations, localized deformations within the body part, and so forth) between acquisition times.

Registration of images may be implemented between the reference imaging system 102 and the IGRT delivery system 104 and/or between the data and/or images derived from the various modalities of the multimodal IGRT delivery system 104, including the low energy source(s) 110 and the high energy source 108 (and their associated detectors 112). In particular, referring back to apparatus 10, registration may be implemented between data and/or images derived from radiation sources 20, 30 and detectors 24, 34.

Figure 4:
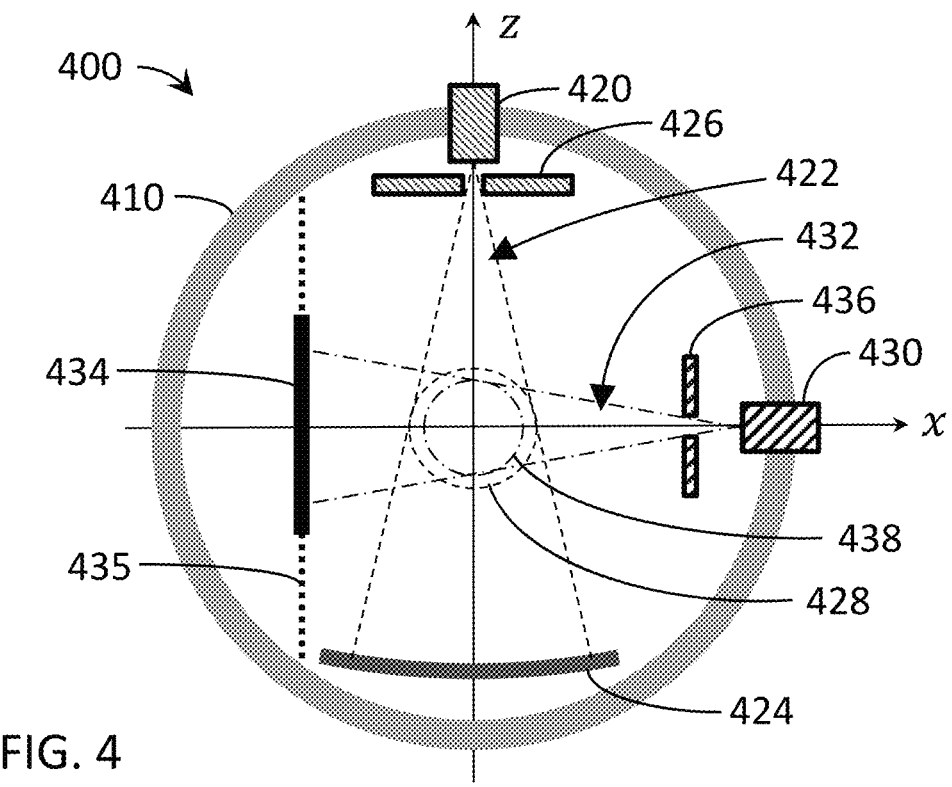
FIG. 4 shows an illustration of an exemplary multimodal scan configuration.

In one embodiment, FIG. 4 shows an illustration of an exemplary multimodal scan configuration 400. Looking into the front of the ring gantry 410, FIG. 4 shows a high energy radiation source 420 (e.g., MV) and a low energy radiation source 430 (e.g., kV) mounted to the ring gantry 410. Radiation sources 420, 430 are shown mounted orthogonal to each other, but other embodiments can include other angular relationships and additional radiation sources and/or detectors. High energy radiation source 420 is shown projecting radiation through a beamformer 426 to create radiation beam 422 projecting onto a portion of detector 424. In this configuration, high energy radiation source 420 has transaxial field of view (FOV) 428. Low energy radiation source 430 is shown projecting radiation through a beamformer 436 to create radiation beam 432 projecting onto a portion of detector 434. In this configuration, low energy radiation source 430 has transaxial FOV 438. Detector 434 is shown centered within its range 435. In this manner, the radiation sources 420, 430 will project radiation through an overlapping transaxial FOV. In this embodiment, the multimodal scan configuration 400 shows the high energy FOV 428 with a larger transaxial FOV than the low energy FOV 438.

Figure 5:
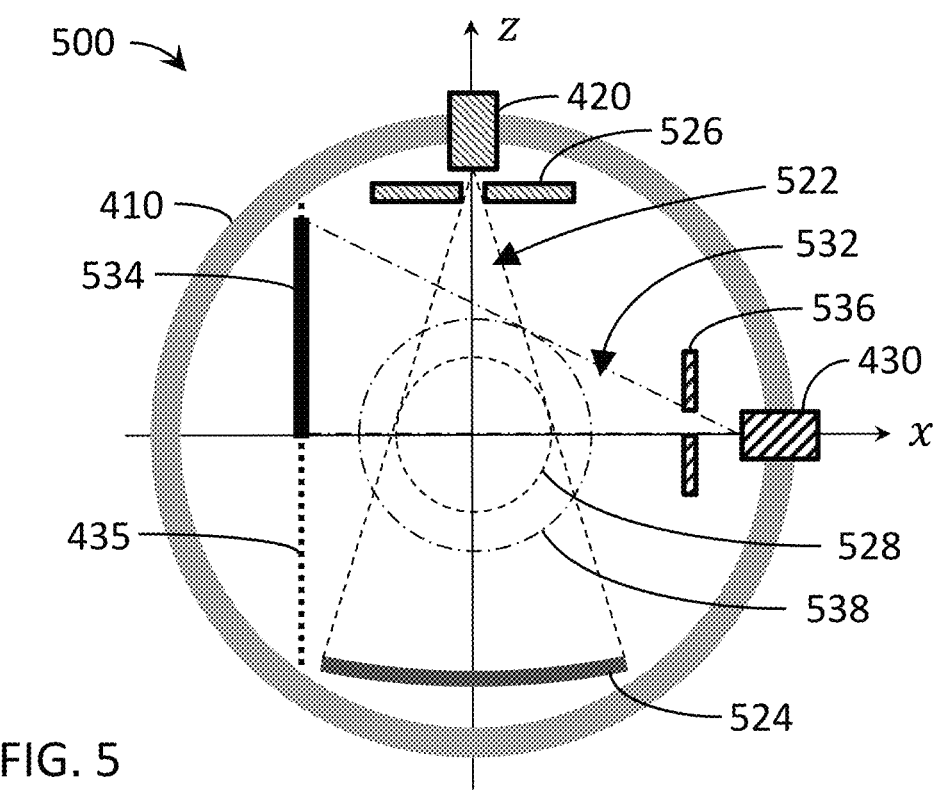
FIG. 5 shows an illustration of another exemplary multimodal scan configuration.

In another embodiment, FIG. 5 shows an illustration of another exemplary multimodal scan configuration 500. Looking into the front of the ring gantry 410, FIG. 5 also shows the high energy radiation source 420 and the low energy radiation source 430 mounted orthogonally to the ring gantry 410. High energy radiation source 420 is shown projecting radiation through a beamformer 526 to create radiation beam 522 projecting onto detector 524. In this configuration, high energy radiation source 420 has transaxial FOV 528. Low energy radiation source 430 is shown projecting radiation through a beamformer 536 to create radiation beam 532 projecting onto offset detector 534. In this configuration, low energy radiation source 430 has transaxial FOV 538 with at least 180 degrees of rotation. In this manner, the radiation sources 420, 430 will also project radiation through an overlapping transaxial FOV. In this embodiment, the multimodal scan configuration 500 shows the low energy FOV 538 with a larger transaxial FOV than the high energy FOV 528.

Various factors, including, for example, beamformer configurations, radiation source angles, detector positions, etc. may be used to control the respective FOVs (e.g., transaxial and axial) of the radiation sources. In some embodiments, the radiation sources 420, 430 may be physically offset in the longitudinal direction (along the y-axis) and may scan the patient at different times (temporally offset).

Figure 6:
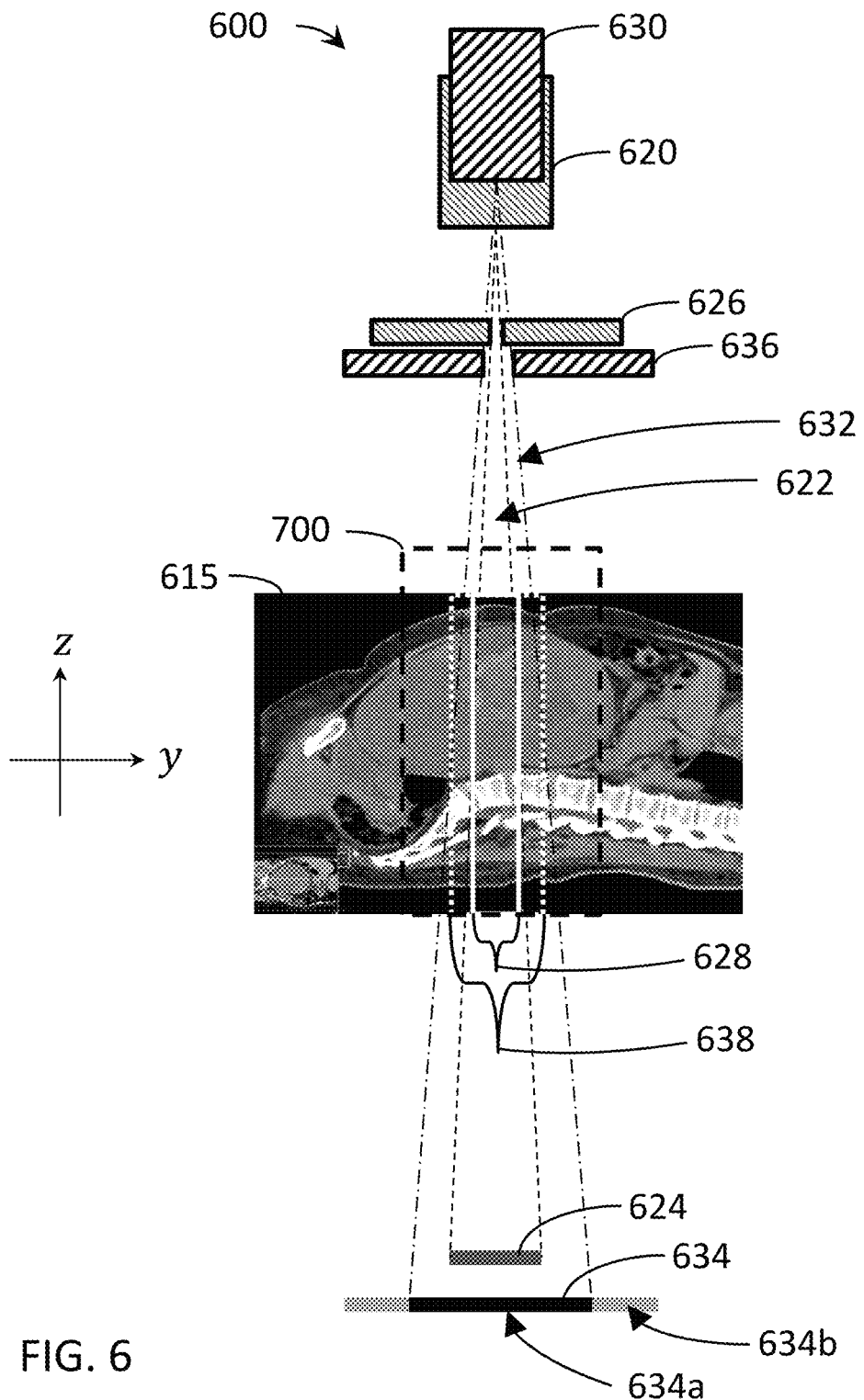
FIG. 6 shows an illustration of exemplary modalities of a multimodal scan configuration in a superimposed view.

In another embodiment, FIG. 6 shows an illustration of exemplary modalities of a multimodal scan configuration 600 with a superimposed view. Looking into the side of the ring gantry (not shown), FIG. 6 shows the position of a high energy radiation source 620 (e.g., MV) and a low energy radiation source 630 (e.g., kV) superimposed into the same plane of a target 615. Radiation sources 620, 630 are not typically mounted against each other and may be mounted to the gantry 90 degrees apart, but are shown superimposed in FIG. 6 to show an exemplary overlap of their respective view and features. Other embodiments can include other angular relationships and additional radiation sources. High energy radiation source 620 is shown projecting radiation through a beamformer 626 to create radiation beam 622 projecting onto a detector 624. In this configuration, high energy radiation source 620 has axial FOV 628. Low energy radiation source 630 is shown projecting radiation through a beamformer 636 to create radiation beam 632 projecting onto a portion of detector 634. In this configuration, low energy radiation source 630 has axial FOV 638. Detector 634 is shown with active region 634a receiving direct projections and shadowed region 634b blocked from direct radiation by beamformer 636. In this manner, the radiation sources 620, 630 will project radiation through an overlapping axial FOV. In this embodiment, the multimodal scan configuration 600 shows the low energy FOV 638 with a larger axial FOV than the high energy FOV 628.

Figure 7:
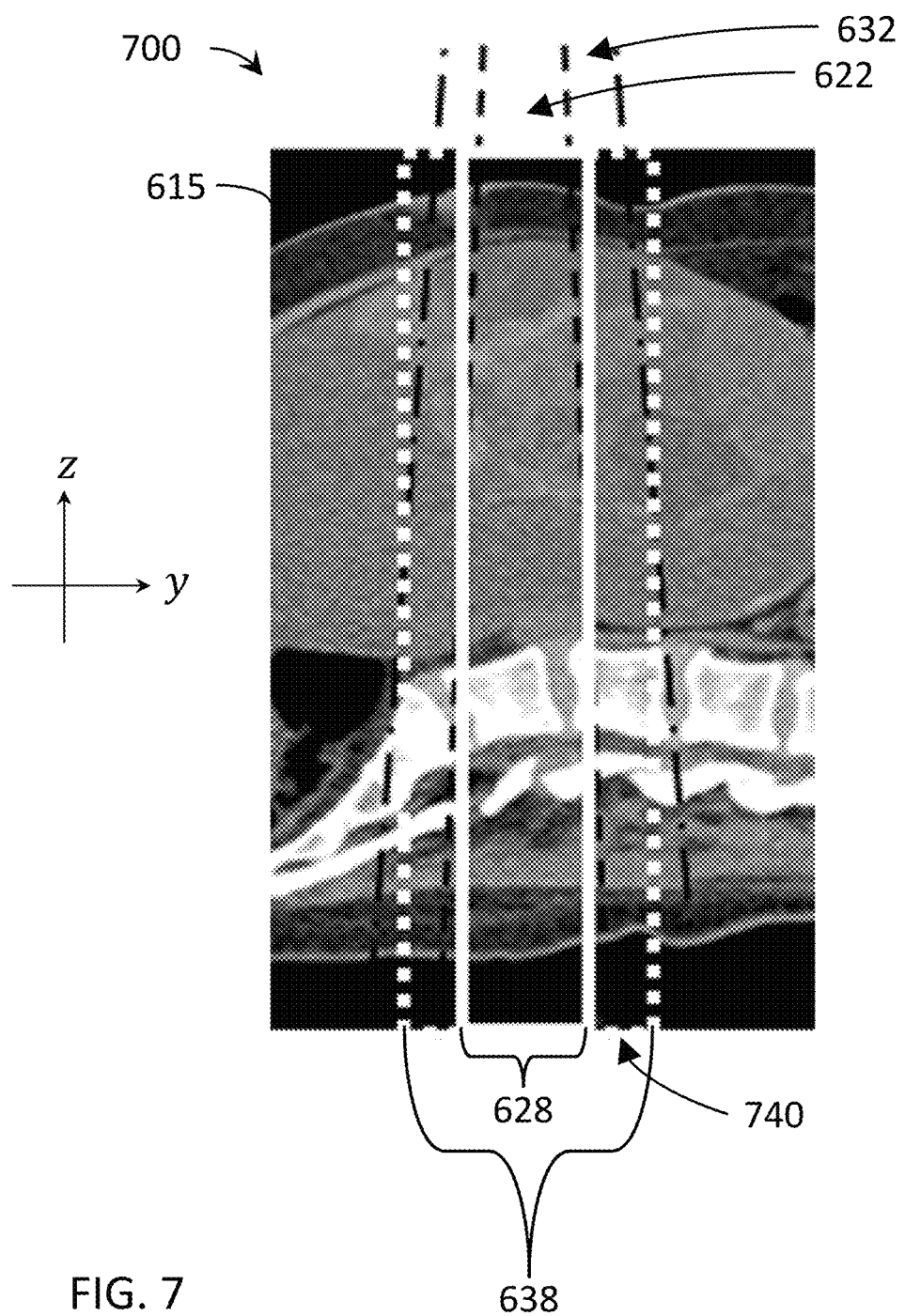
FIG. 7 shows an illustration of a zoomed-in portion of the target shown in FIG. 6.

FIG. 7 shows a zoomed-in portion 700 of the target 615 shown in FIG. 6. Radiation beams 622, 632 are shown passing through target 615. High energy FOV 628 and low energy FOV 638 provide overlapping imaging data. Here, the low energy FOV 638 provides imaging data beyond the high energy FOV 628, shown as area 740. However, in other embodiments, as described above, the high energy FOV 628 can provide imaging data beyond the low energy FOV 638. In some embodiments, the FOVs 628, 638 may be the same (e.g., transaxially and/or axially). In still further embodiments, the FOVs 628, 638 may be adjacent but not overlap, may have space between, may be banded such that one FOV is within the other without overlap, etc., and combinations thereof.

In some embodiments, one or more of the radiation sources may be used for sparse data, may utilize different resolutions, speeds, trajectories, frequencies, power levels, dosages, FOVs, etc. In any event, data from two or more radiation modalities can be used in combination to improve image quality, speed, dosing, workflow, treatment accuracy/precision, etc.

In various embodiments, the exemplary scan configurations 400, 500, 600 may be implemented using multimodal apparatus 10, including via radiation treatment environment 300.

The following flow charts and block diagrams illustrate exemplary configurations and methodologies associated with the multimodal radiation systems described above. The exemplary methodologies may be carried out in logic, software, hardware, or combinations thereof. In addition, although the procedures and methods are presented in an order, the blocks may be performed in different orders, including series and/or parallel. Further, additional steps or fewer steps may be used.

Figure 8:
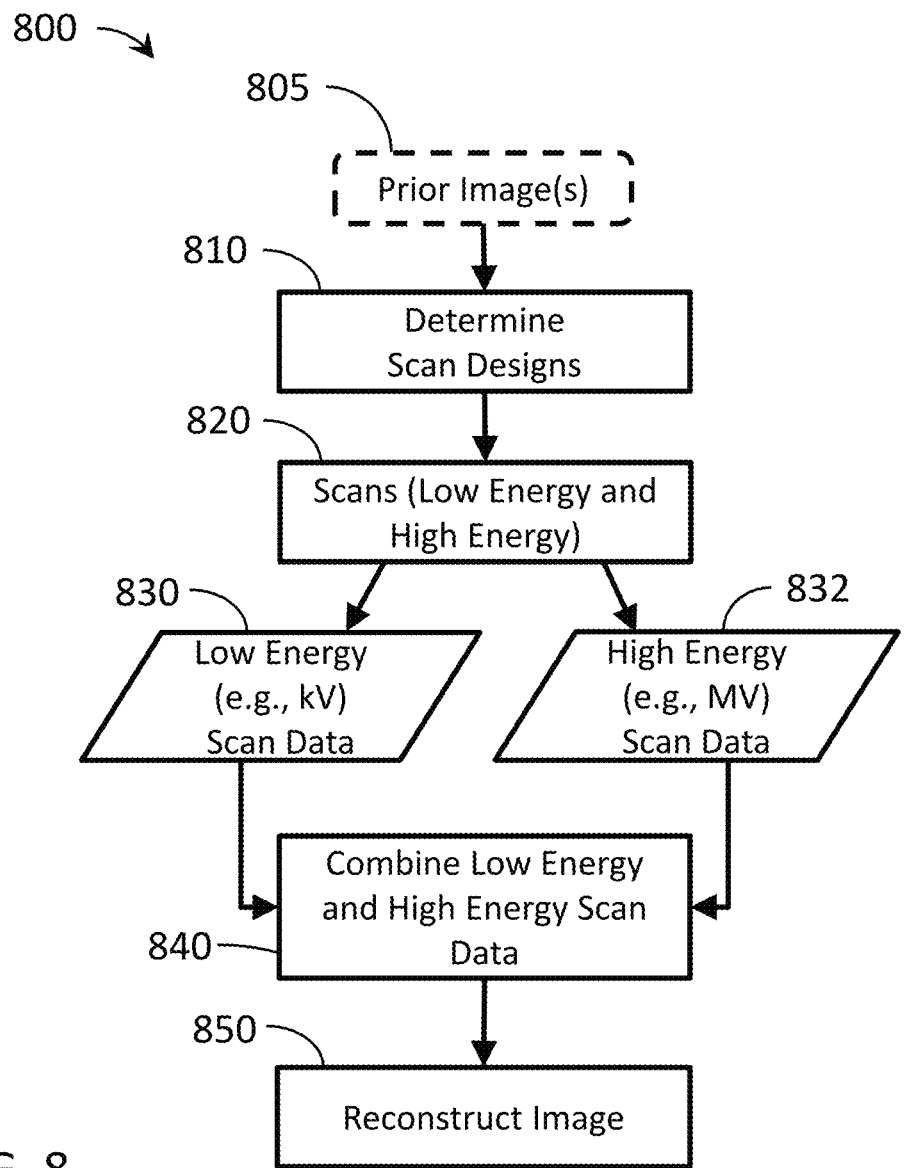
FIG. 8 is a flow chart depicting an exemplary method of combining scan data from multiple radiation modalities.

FIG. 8 is a flow chart depicting an exemplary method 800 of combining scan data from multiple radiation modalities, such as those described above. At step 805, prior image data 805 may be provided. At step 810, the method 800 determines a scan configuration, including scan designs for each modality of the multimodal system. Then at step 820, the scans are executed, including, for example, a low energy kV scan and a high-energy MV scan, as described above. The scans produce low energy scan data 830 and high energy scan data 832. Next, at step 840, the method 400 makes use of or combines the low energy scan data 830 and the high energy scan data 832. Then at step 850, the method 800 processes a combined data set, for example, to reconstruct an image. In this manner, generally, the scan configuration and associated scan designs can be configured such that at least one of the scan data 830, 832 complements or supplements another of the scan data 830, 832 from a different modality to yield at least one of the improvements discussed herein.

In some embodiments, the scan configuration includes a helical scan trajectory. A helical fan-beam MV (high energy) CT (MVCT) acquisition geometry can provide several advantages, including, for example, a wide transverse view (e.g., about 40 cm at the isocenter), complete Fourier sampling of the volume of interest, and decreased scatter fraction in projection images. These features can improve the quality of the reconstructed image over clinical state-of-the-art cone-beam MVCTs. In particular, for example, a source of these advantages is the fan-collimated MV treatment/imaging beam and the fact that the MV source and detectors are mounted on a continuously rotating slip-ring system that is capable of imaging from all directions, as described above. In operation, the system (e.g., apparatus 10) can image continuously over more than $2\pi$ radians, moving the source and detector in a helical trajectory with respect to a patient on a translating couch without stopping to unwind cabling or resorting to atypical imaging trajectories.

In various embodiments, in addition to the helical fan-beam MVCT system, a kV (low energy) X-ray source and flat panel detector allows the system to acquire kV CT (kVCT) images with the following geometries: helical fan-beam; helical narrow cone angle cone-beam; and stationary-couch, circular trajectory fan-beam, etc., as described above. Because the kV imaging hardware is mounted to the same slip-ring gantry as the MV imaging/therapy hardware (e.g., as shown in FIGS. 2 and 4-6), the kV imaging system also can take advantage of the slip-ring mounted imaging system, as described above, allowing the kV imaging system to operate as a diagnostic CT, rather than a positioning CBCT, as is found in traditional C-arm systems.

A further unique benefit of a multimodal (e.g., dual kV/MV), slip-ring mounted imaging systems (e.g., apparatus 10) is that the systems, being mounted together (e.g., orthogonal to each other), can be used to acquire image data that are exactly synchronized in time and space. Both the MV and kV systems can image the same anatomy at the same time producing simultaneous acquisitions of the patient's anatomy (e.g., as shown in FIGS. 6-7), including 3-D information as it changes over time. Although the projection angles for each of the systems may be different, this does not present a problem with complete CT imaging of the subject and the symmetry inherent in CT reconstruction. Combined with the fast imaging speed due to slip-ring mounting, the system can quickly acquire high temporal resolution kV/MV fan beam images over a long axial extent.

In various embodiments, the multimodal apparatus 10 can include N-tuple source and detector CT systems (where N sources and N or another number of detectors are positioned such that their respective projection image data can be acquired simultaneously) with sources providing multi-energetic (e.g., low energy and high energy) projection data. Combining the use of fan-beam imaging geometries (e.g., using helical scan trajectories) with simultaneous multi-energetic kV/MV imaging devices yields the advantages described herein. Typical existing systems are limited to cone-beam imaging geometries for either kV or MV sources individually, which have noticeable disadvantages over fan-beam imaging geometries, as described above.

In various embodiments, high energy MV fan-beam projections and low energy kV fan-beam or cone-beam projections can be used in simultaneous CT reconstructions. In some embodiments, the MV projections can be used as a priori information to amend artifacts of the kVCT, or used in a dual-energy CT reconstruction for quantitative imaging and material separation. Furthermore, MLC-modulated MV projection data is available during treatment and may be leveraged in kVCT reconstructions concurrent with or following treatment delivery. The kV acquisition can be concurrent with and/or preceding treatment. Electron density images obtained from dual-energy reconstructions can be used in both online and offline dosimetry applications.

Several issues that arise in known medical imaging and/or radiation treatment systems are at least partially addressed by one or more of the embodiments described herein. For example, increasing the precision of spatial registrations between respective image sets to allow more precise radiation treatment delivery, reducing image artifacts (e.g., scatter, metal and beam hardening, image blur, motion, etc.), and utilization of dual energy imaging (e.g., for material separation and quantitative imaging, patient setup, online adaptive IGRT, etc.).

I. A.

In some embodiments, a multimodal apparatus can be utilized for scatter correction. With reference to the multimodal apparatus 10 of FIG. 2, in one embodiment, a flat panel kV detector 34 and a (e.g., Xenon gas) MV detector 24 are sensitive to both kV and MV energies. Each detector 24, 34 is therefore capable of measuring the orthogonal body scatter during exposure by the other source 20, 30. For example, the MV detector 24 can measure kV scatter over a single but wide row of detectors, while the kV detector 34 can measure an object scatter field over an area of, for example, 40 cm by 40 cm. In other embodiments, the MV detector 24 need not be a single row, nor wide.

In some embodiments, one detector may be used instead of separate detectors 24, 34. For example, the kV and MV radiation sources could be located adjacent to each other on a ring gantry. Then a detector sensitive to both kV and MV radiation could be located on the opposite side of the gantry. The detector could be actuated to move between at least two positions to receive either kV or MV radiation passing through the isocenter of the system depending on the position of the detector. Alternately, a wide detector that is wide enough to measure radiation from the entirety of both the kV and MV beams simultaneously could be used. A less wide detector could also be used, but may have only a limited field of view from each radiation beam, These scatter measurements, potentially with the addition of training data from known objects, can be used to improve the scatter correction in the corresponding images. For example, although the MV scatter is low enough to be ignored in the MVCT image chain, non-negligible CT inaccuracies and non-uniformities in the MVCT images may be attributable to an uncorrected scatter signal. The kVCT, and in particular a kV cone beam CT, can be affected by a much larger scatter signal in the measured projections. The MV detector measurement of the orthogonal kV scatter can be utilized to better estimate and differentiate the scatter contribution from the object in the bore, leading to improved uniformity and low contrast resolution in the kVCT images.

Figure 9:
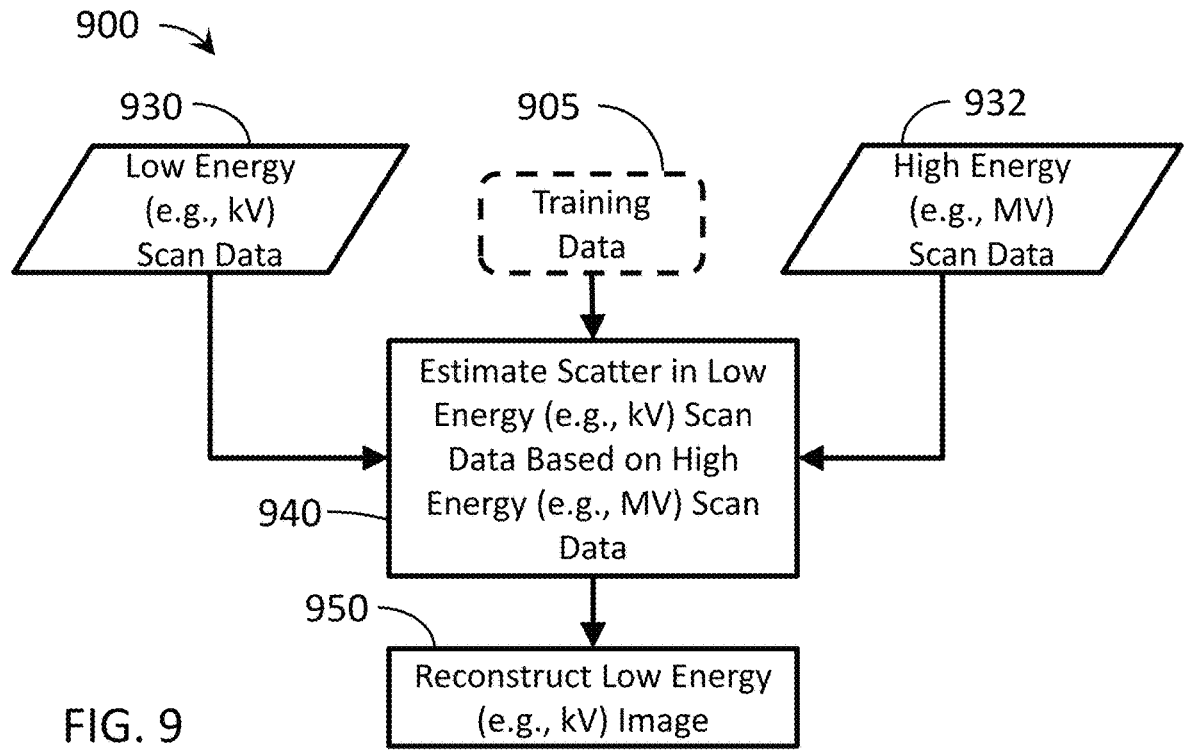
FIG. 9 is a flow chart depicting an exemplary method of combining scan data from multiple radiation modalities for scatter correction.

For example, FIG. 9 is a flow chart depicting an exemplary method 900 of combining scan data from multiple radiation modalities for scatter correction. Training data 905 from known objects, models, etc. may be provided to improve the process. In some embodiments, a scan configuration (including scan designs for each modality of the multimodal system) may be determined and scans executed according to method steps 810 and 820 of method 800 to generate the scan data 930, 932. The low energy scan data 930, for example, may be from a low energy kV scan and has a relatively high scatter ratio. The high energy scan data 932, for example, may be from a high-energy wide-field MV fan-beam scan and has a relatively low scatter ratio. Both projections are in the same transverse plane(s) of the same object scene. At step 940, the method 900 makes use of or combines the low energy scan data 930 and the high energy scan data 932 by estimating the scatter in the low energy kV scan data 930 based on the corresponding high energy MV scan data 932. In other embodiments, the MV detector can also provide "blank" projections or scans, in which the kV scatter signal is measured in the absence of MV x-rays. Then at step 950, the method 900 reconstructs the low energy kV image using the scatter estimate.

In some embodiments, the MV and kV projections are acquired simultaneously or within a short interval, such as, for example, less than 50 ms. In some embodiments, the MV beam 22 forming the MV images has a relatively low probability of scatter interaction. In some embodiments, the kV beam 32 forming the kV images has a relatively high probability of scatter interaction. The relative probabilities can be associated with the scatter mechanisms which fundamentally differentiate the low-energy and high-energy radiation (e.g., photoelectric+Compton versus Compton-only). Compton-only can be applicable to a high-energy radiation source (e.g., MV). A low-energy radiation source (e.g., kV) may also be subject to photoelectric interactions.

I. B.

In some embodiments, a multimodal apparatus can be utilized for metal and beam hardening artifact reduction. With reference to the multimodal apparatus 10 of FIG. 2, in one embodiment, under kV exposure from kV source 30, rays from beam 32 passing through metal (such as, e.g., dental or other surgical implants) or otherwise highly attenuating objects (such as, e.g., dense bone or calcifications) can block all or nearly all of the signal from reaching detector 34 (preferentially attenuating lower energy photons over higher energy photons) along rays passing through the highly attenuating material. This can lead to an undefined, highly uncertain, or otherwise artefactual measurement of the attenuation along those rays by detector 34, leading to streaking artifacts passing though the object. These artifacts are energy dependent, such that they are less pronounced when imaged with higher energy photons, for example, from a MV source 20. For example, a highly attenuated object may block about 70% of a kV signal, but only about 7% of a MV signal, about a ten times difference. However, higher energy photons (from MV source 20) result in less inherent attenuation contrast in biological tissues than lower energy photons (from kV source 30). In order to correct for these artifacts while maintaining soft-tissue contrast, sparse projection data or reconstructed images from an MVCT system (including MV source 20 and detector 24) can be used to fill in the missing information and reduce the artifacts in a kVCT system (including kV source 30 and detector 34).

Figure 10:
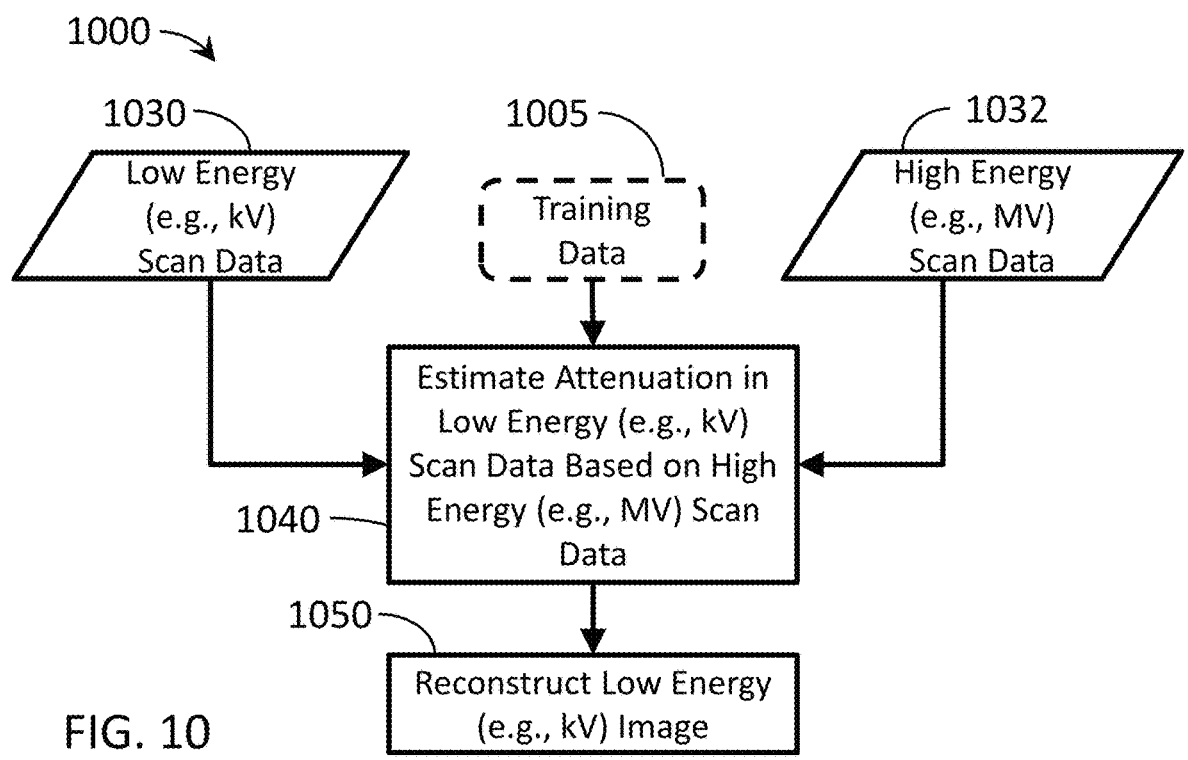
FIG. 10 is a flow chart depicting an exemplary method of combining scan data from multiple radiation modalities for metal and beam hardening artifact reduction.

For example, FIG. 10 is a flow chart depicting an exemplary method 1000 of combining scan data from multiple radiation modalities for metal and beam hardening artifact reduction. Training data 1005 from known objects, models, etc. may be provided to improve the process. In some embodiments, a scan configuration (including scan designs for each modality of the multimodal system) may be determined and scans executed according to method steps 810 and 820 of method 800 to generate the scan data 1030, 1032. The low energy scan data 1030, for example, may be from a low energy kV scan and has relatively high attenuation, for example, dominated by photoelectric absorption, as mentioned above. The high energy scan data 1032, for example, may be from a high-energy wide-field MV fan-beam scan and has a relatively low known attenuation, dominated by a different physical mechanism—Compton scattering. Both projections are in the same transverse plane(s) of the same object scene. At step 1040, the method 1000 makes use of or combines the low energy scan data 1030 and the high energy scan data 1032 by estimating the attenuation of a kV projection in the low energy kV scan data 1030 passing through dense structures dominated by photoelectric absorption based on the corresponding high energy MV scan data 1032. Then at step 1050, the method 1000 reconstructs the low energy kV image using the attenuation estimate.

In some embodiments, the MV and kV projections are acquired simultaneously or within a short interval, such as, for example, less than 50 ms. In some embodiments, the MV beam 22 forming the MV images has a peak energy of about 3 MeV and an average energy of about 1 MeV. In some embodiments, the kV beam 32 forming the kV images has a peak energy of less than or equal to 150 keV.

I. C.

In some embodiments, a multimodal apparatus can be utilized for time resolution correction (e.g., image blur correction). With reference to the multimodal apparatus 10 of FIG. 2, in one embodiment, MV projections from MV source 20 are sharply time resolved (e.g., about 5 µs), and therefore sharply resolved in gantry angle, compared to kV projections from kV source 30 (e.g., about 10 ms). Furthermore, the achievable pulse rate is higher for a MV beam 22 (e.g., up to 300 Hz) than a typical pulse rate for a kV beam 32 of a kV-CBCT system (e.g., about 15 Hz). The blur in the kV projections, whether by continuous or pulsed exposure, increases with exposure time and gantry rate. In one embodiment, the extent of the blur on the detector 34 may be, for example, about 10 pixels, based on the geometry and kV operation, and may require 2D correction or 3D modeling. For example, in a model-based 3D solution, the MV projections can provide time-resolved information to improve the consistency of the model-based reconstruction, or to regularize the 2D deblurring operator.

Figure 11:
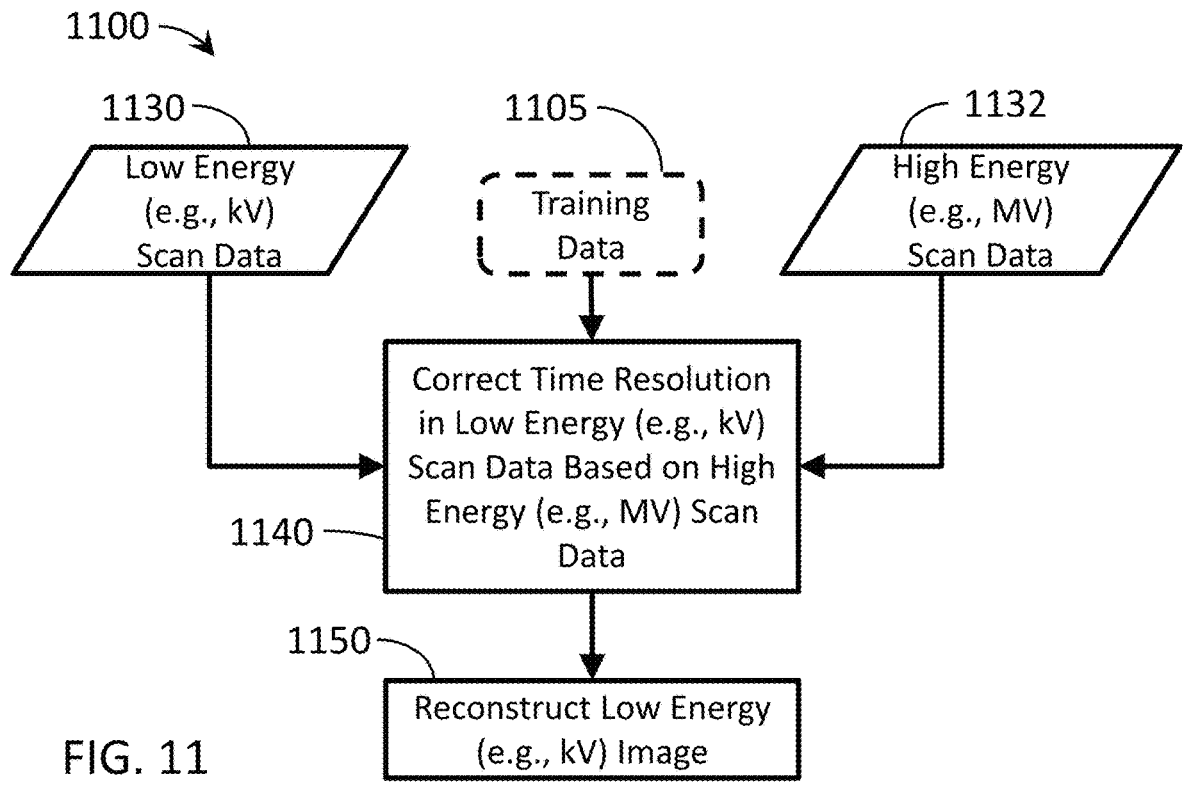
FIG. 11 is a flow chart depicting an exemplary method of combining scan data from multiple radiation modalities for time resolution correction.

For example, FIG. 11 is a flow chart depicting an exemplary method 1100 of combining scan data from multiple radiation modalities for time resolution correction (e.g., image blur correction for lung or cardiac imaging). Training data 1105 from known objects, models, etc. may be provided to improve the process. In some embodiments, a scan configuration (including scan designs for each modality of the multimodal system) may be determined and scans executed according to method steps 810 and 820 of method 800 to generate the scan data 1130, 1132. The low energy scan data 1130, for example, may be from a low energy kV scan and has a relatively low pulse rate (e.g., slow integration). For example, typical kV integration times may be 5-20 ms. However, since pulse rate is 1/cycle period, which includes detector read-out time, it may have a range of 10-100 ms. The high energy scan data 1132, for example, may be from a high-energy MV scan and has a relatively high pulse rate (e.g., fast integration). For example, typical MV integration times may be 1-10 us. The cycle time for the MV system is not limited by integration time. In one embodiment, a rate of up to 300 Hz is used with a cycle time of 3.3 ms. At step 1140, the method 1100 makes use of or combines the low energy scan data 1130 and the high energy scan data 1132 by using the MV scan data 1132 with higher temporal discrimination to assist the interpolation of the kV scan data 1130 with a better spatial image having fewer time point estimates for image blur correction. Then at step 1150, the method 1100 reconstructs the low energy kV image using the image blur correction, e.g., for a sharp time-resolution motion deblurred image.

In some embodiments, the high energy scan is a MV fan-beam CT and the low energy scan is a kV narrow beam CT. In some embodiments, the high energy scan is a MV fan-beam CT and the low energy scan is a kV cone-beam CT.

I. D.

In some embodiments, a multimodal apparatus can be utilized for motion artifact correction. With reference to the multimodal apparatus 10 of FIG. 2, in one embodiment, as discussed above, MV projections from MV source 20 are much more sharply time-resolved than kV projections from kV source 30.

Figure 12:
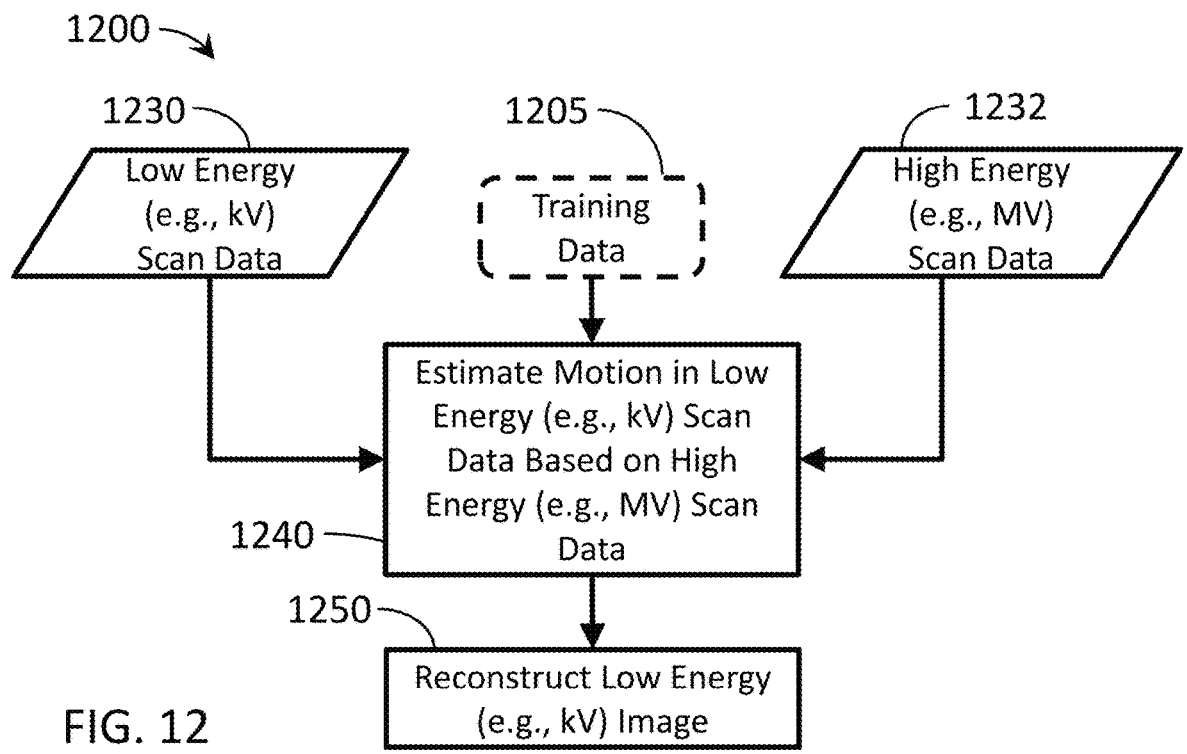
FIG. 12 is a flow chart depicting an exemplary method of combining scan data from multiple radiation modalities for motion artifact correction.

For example, FIG. 12 is a flow chart depicting an exemplary method 1200 of combining scan data from multiple radiation modalities for motion artifact correction. Training data 1205 from known objects, models, etc. may be provided to improve the process. In some embodiments, a scan configuration (including scan designs for each modality of the multimodal system) may be determined and scans executed according to method steps 810 and 820 of method 800 to generate the scan data 1230, 1232. The low energy scan data 1230, for example, may be from a low energy kV scan and less sharply time resolved (e.g., low frequency). The high energy scan data 1232, for example, may be from a high-energy MV scan and is more sharply time resolved (e.g., high frequency). At step 1240, the method 1200 makes use of or combines the low energy scan data 1230 and the high energy scan data 1232 by using the MV scan data 1232 with more sharply time resolved projections to estimate motion for use in motion correction of the kV scan data 1230 with motion artifacts. For example, in one embodiment of step 1240, the method 1200 combines low frequency kV scan data 1230 and high frequency MV scan data 1232 to build a correlation model between high frequency MV scan data 1232 and the combined image data, then uses the high frequency MV scan data 1232 to interpolate high frequency motion included in the low frequency kV projection data 1230 based on the correlation model 1240. Then at step 1250, the method 1200 reconstructs the low energy kV image using the motion correction. In another embodiment, step 1250 can otherwise include reconstructing a high frequency motion trace. In other embodiments, in addition to having different projection frequencies for the low energy scan data 1230 and high energy scan data 1232, projection integration times may be different. For example, low energy scan data 1230 (e.g., kV projections) may have a longer integration time (e.g., 5-30 ms) while high energy scan data 1232 (e.g., MV projections) may have a shorter integration time (e.g., ~0.001 ms). In these embodiments, the high energy scan data 1232 can be used to remove rotational or motion blurring inherent in the low energy scan data 1230.

In various embodiments, the high energy scan is a MV scan (e.g. a MV fan-beam CT) and the low energy scan is a kV scan (e.g., a kV narrow beam CT or a kV cone-beam CT). In various embodiments, the viewing angle between the high energy source 20 and the low energy source 30 is orthogonal. In one embodiment, a motion correction is based on the motion estimate (which is based on the 3D reconstruction) and applied as a real-time adjustment to the second radiation source, (e.g., orientation, collimation, and/or gating for uncontrolled motions, etc.) while simultaneously using the second radiation source to deliver therapeutic radiation.

II. A.

In some embodiments, a multimodal apparatus can be utilized for material separation and/or quantitative imaging. With reference to the multimodal apparatus 10 of FIG. 2, in various embodiments, MV projections from MV source 20 and kV projections from kV source 30 can be acquired in a simultaneous, interleaved, or serial manner. Images derived from different energy spectra (e.g., high energy source 20 and low energy source 30) provide linearly independent measurements of material properties. Generally, more accurate mass/electron density estimations can be obtained from MV images than from kV images, but kV-kV registration is likely to be more accurate than kV/MV registration. In various embodiments, these differences can be used to decompose projections and voxels into a linear combination of two basis materials (e.g., "soft tissue" and "bone"). By altering the contributions of a basis material, one material can be suppressed while the other can be enhanced, leading to increased image quality.

Figure 13:
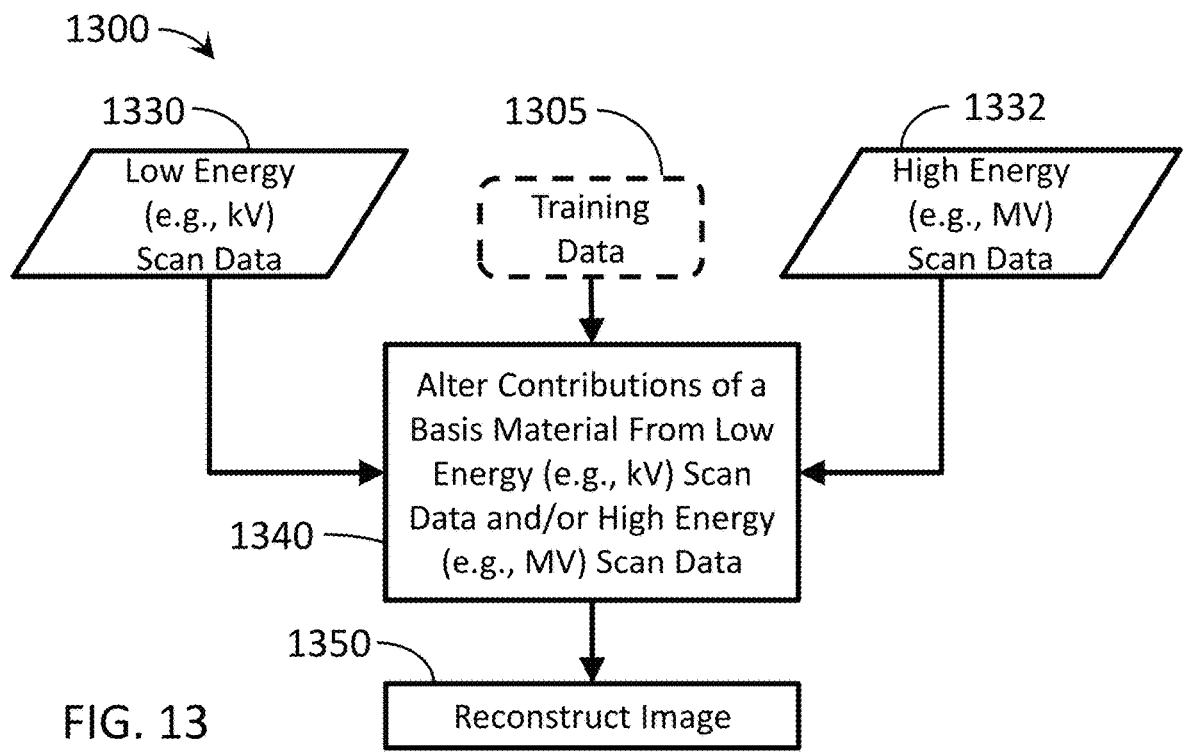
FIG. 13 is a flow chart depicting an exemplary method of combining scan data from multiple radiation modalities for material separation and/or quantitative imaging.

For example, FIG. 13 is a flow chart depicting an exemplary method 1300 of combining scan data from multiple radiation modalities for material separation and/or quantitative imaging. Training data 1305 from known objects, models, etc. may be provided to improve the process. In some embodiments, a scan configuration (including scan designs for each modality of the multimodal system) may be determined and scans executed according to method steps 810 and 820 of method 800 to generate the scan data 1330, 1332. The low energy scan data 1330, for example, may be from a low energy kV scan. The high energy scan data 1332, for example, may be from a high-energy MV scan, where the MV scan data 1332 and the low energy scan data 1330 provide linearly independent measurements of at least one material property of the object. At step 1340, the method 1300 alters a contribution of at least one basis material from at least one of the scan data 1330, 1332. Then at step 1350, the method 1300 reconstructs an image using the altered contribution of at least one basis material.

In one embodiment, altering a contribution of at least one basis material from at least one of the scan data 1330, 1332 provides a quantitative image of electron density. In some embodiments, the low energy scan data 1330 comprises projection data associated with at least two spectrally separated keV energies.

II. B.

In some embodiments, a multimodal apparatus can be utilized for patient setup. With reference to the multimodal apparatus 10 of FIG. 2, in one embodiment, 2D dual-energy images (e.g., from high energy source 20 and low energy source 30) can be used in a 2D image registration workflow, for example to toggle off bones or soft-tissue. In one embodiment, the registration scan could be a low-dose, two-angle, two-energy scout scan, with the return scan at a 90 degree gantry shift such that MV and kV projection pairs are available from two angles in each plane. Only one of these angles would have matching ray angles, due to an exemplary fixed 90 degree offset of the MV and kV sources. The second angle would obtain only non-complementary fan data from opposing sides of the gantry 12.

Figure 14:
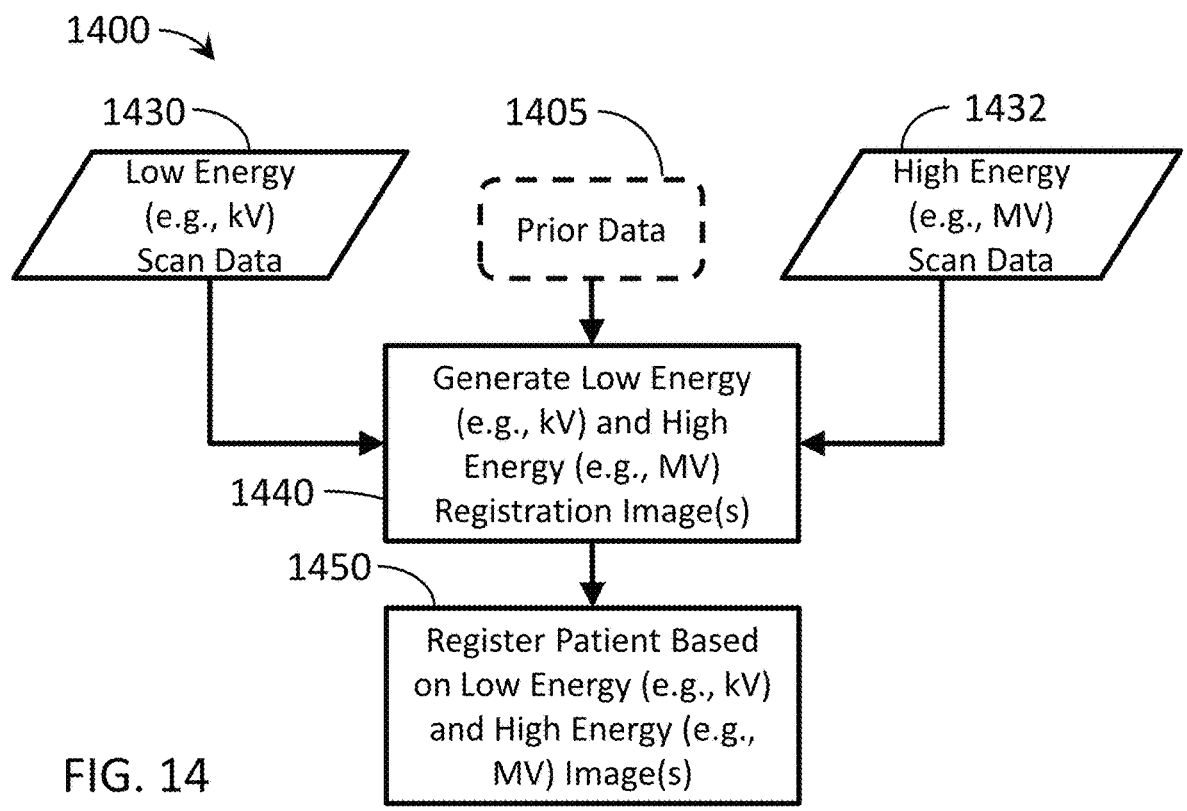
FIG. 14 is a flow chart depicting an exemplary method of combining scan data from multiple radiation modalities for patient setup.

For example, FIG. 14 is a flow chart depicting an exemplary method 1400 of combining scan data from multiple radiation modalities for patient setup. Prior data 1405 is from known prior images, objects, models, etc. In some embodiments, a scan configuration (including scan designs for each modality of the multimodal system) may be determined and scans executed according to method steps 810 and 820 of method 800 to generate the scan data 1430, 1432. The low energy scan data 1430, for example, may be from a low energy kV scan. The high energy scan data 1432, for example, may be from a high-energy MV scan. In this embodiment, the high energy scan and the low energy scan are concurrent and the high energy source 20 and low energy source 30 are orthogonal as part of a scout scan workflow. At step 1440, the method 1400 makes use of or combines the low energy scan data 1430 and the high energy scan data 1432 to generate registration image(s). Then at step 1450, the method 1400 registers the patient based on the low energy and high energy image(s).

In some embodiments, the scout scan is bidirectional to acquire dual energy projections from the same gantry angles. In some embodiments, geometrically coincident dual energy projections are used for material separation in the registration workflow.

II. C.

In some embodiments, a multimodal apparatus can be utilized for online adaptive IGRT, as well as offline adaptive IGRT and delivery quality assurance. With reference to the multimodal apparatus 10 of FIG. 2, in one embodiment, online 3D kVCT uses a kV subsystem (including, e.g., low energy source 30, beamformer 36, and detector 34) for online 3D motion adaptation. This embodiment also includes using MV treatment beam 22 projection data to both improve the image quality at the planning target volume (PTV) and to use it as a constraint on the quantitative image of electron density. Here, the MV exit detector 24 data is leveraged in a dual-energy iterative reconstruction by forward projecting the MLC aperture in the MVCT geometry and enforcing projection data consistency. For example, there can be 51 MLC apertures per rotation and the high energy MV source 20 can be pulsed at 300 Hz, resulting in a high number of detector counts with image information focused to the treatment structures. This data could be used to achieve low noise, quantitative images of the treatment areas. Low noise views can enable deformable PTV tracking in addition to rigid motion tracking, such that the plan could be adapted online to the shape and location of the PTV.

Figure 15:
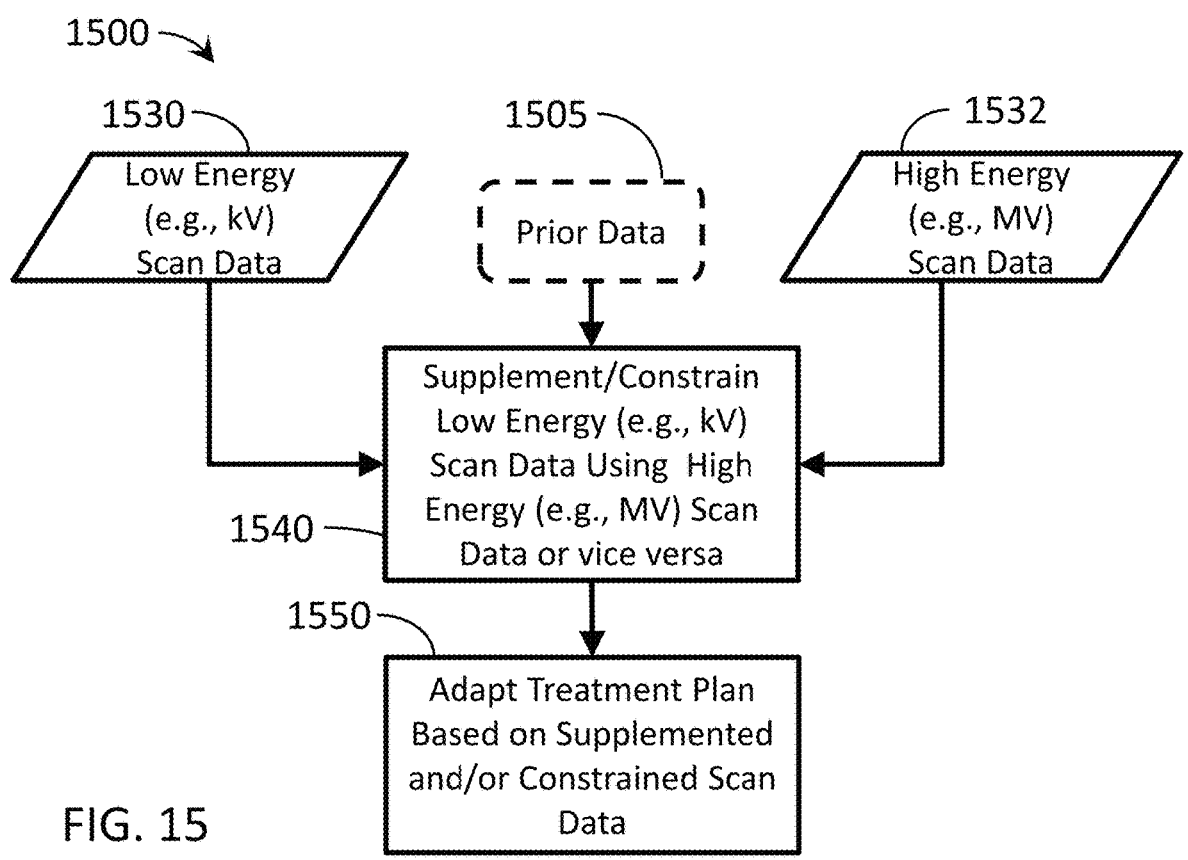
FIG. 15 is a flow chart depicting an exemplary method of combining scan data from multiple radiation modalities for online adaptive IGRT.

For example, FIG. 15 is a flow chart depicting an exemplary method 1500 of combining scan data from multiple radiation modalities for online adaptive IGRT. Prior data 1505 is from known prior images, treatment plans, objects, models, etc. In some embodiments, a scan configuration (including scan designs for each modality of the multimodal system) may be determined and scans executed according to method steps 810 and 820 of method 800 to generate the scan data 1530, 1532. The low energy scan data 1530, for example, may be from a low energy kV scan. The high energy scan data 1532, for example, may be from a high-energy MV scan. At step 1540, the method 1500 makes use of or combines the low energy scan data 1530 and the high energy scan data 1532 to supplement and/or constrain the other scan data 1530, 1532. Then at step 1550, the method 1500 adapts the treatment plan based on the supplemented and/or constrained other scan data.

In some embodiments, fluence field modulation imaging includes supplementing missing MV view information with orthogonal kV projections. In some embodiments involving online 3D kV imaging, MV treatment projections are used as constraints on a quantitative image of electron density. In one embodiment, the online quantitative image is used for online dose calculation. In another embodiment, the calculated dose is used in an offline adaptive workflow. In another embodiment, the calculated dose is used in a quality assurance workflow.

In some embodiments, the above methods can be executed simultaneously or in an interleaved manner based on a preferred workflow. For example, a multimodal scan can be performed and the resulting scan data utilized for two or more of the various features and benefits described above.

When the above apparatus and methods are used in the projection domain, it can be applied on each projection view, where each projection view is a planar image. Various embodiments can utilize different scan geometries, detector positioning (including offset detectors), and/or beamformer window shapes.

As is discussed above, aspects of the disclosed technology can be utilized in a radiotherapy device and methods that make use of multimodal radiation sources, including integrated low energy (e.g., kV) and high energy (e.g., MV) sources for use in conjunction with or as part of IGRT. In accordance with one embodiment, the image acquisition methodology can include or otherwise makes use of a helical source trajectory (e.g., a continuous source rotation about a central axis together with longitudinal movement of a patient support through a gantry bore) or a circular scan, together with fast slip ring rotation, for example, to provide kV CT imaging on a radiation therapy delivery platform.

In some embodiments, it will be appreciated that any potential increased scan time associated with multiple beam rotations to complete a volume image can be mitigated or otherwise offset by high kV frame rates, high gantry rates, and/or sparse data reconstruction techniques. It will be further appreciated that the above-described provision of a selectively controllable collimator/beamformer allows for a system where a user can trade off or otherwise vary image acquisition time versus image quality, depending on the specific application and/or clinical need. It also will be appreciated that the radiotherapy delivery device can be controlled to provide half- or single-rotation cone beam CT scans (with potential reduced image quality due to scatter) with fast image acquisition time (e.g., for motion tracking), as well as circular or continuous helical acquisition with a narrow/slit fan beam with longer acquisition time, but increased image quality due to reduced scatter. One or more optimization processes are also applicable to all of the above embodiments to determine scan designs, determine beam positioning, determine readout range, estimate scatter, etc.

Figure 16:
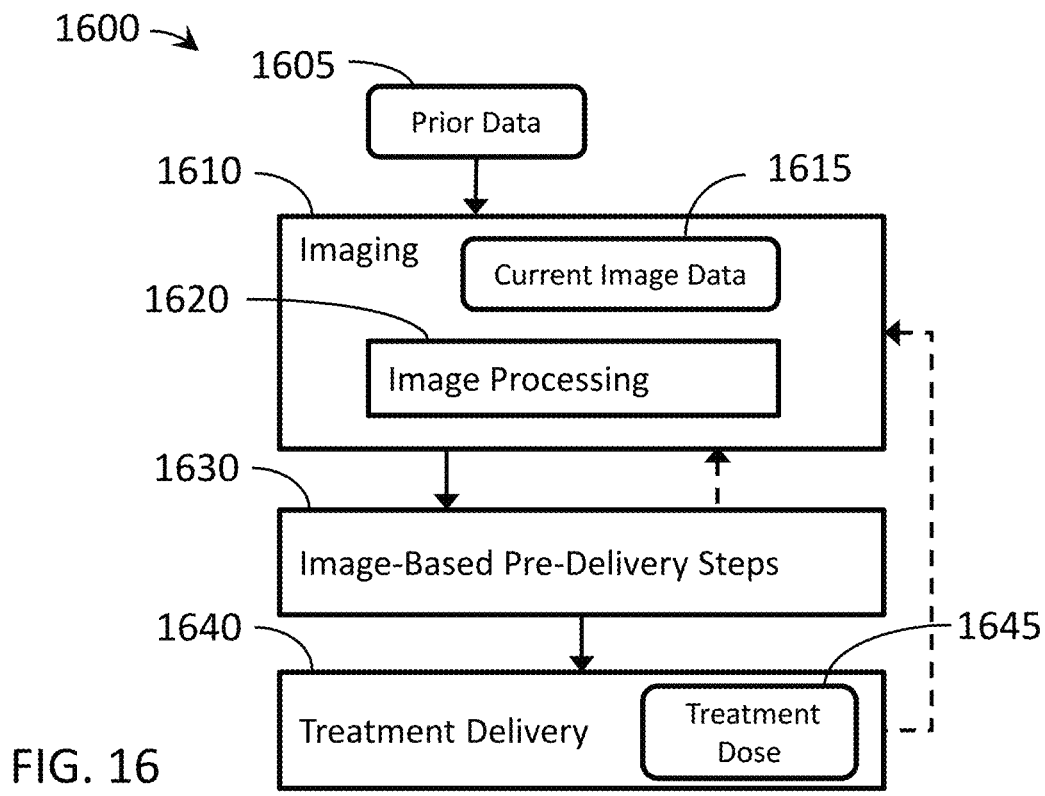
FIG. 16 is a flow chart depicting an exemplary method of IGRT using a radiotherapy device.

FIG. 16 is a flow chart depicting an exemplary method 1600 of IGRT using a radiotherapy device (including, e.g., multimodal apparatus 10). Prior data 1605 can include images of the patient (e.g., a prior image, which may be a previously-acquired planning image, including a prior CT image, as discussed above), treatment plans, phantom information, models, a priori information, etc. In some embodiments, the prior data 1605 is generated by the same radiotherapy device, but at an earlier time. At step 1610, imaging of a patient is performed using a source of radiation (e.g., kV radiation from source 30 and/or MV radiation from source 20 of multimodal apparatus 10). In various embodiments, imaging comprises a helical or circular scan with a fan or cone beam geometry. Step 1610 can produce high-quality (HQ) image(s) or imaging/scan data 1615 using the techniques described above. In some embodiments, image quality may be adjusted to optimize a balance between image quality/resolution and dosage. In other words, not all images need to be of the highest quality or image quality may be adjusted to optimize or trade off a balance between image quality/resolution and image acquisition time. Imaging step 1610 also includes image processing 1620 to generate patient images based on the imaging/scan data 1615 (e.g., in accordance with methods described above). Although image processing step 1620 is shown as part of imaging step 1610, in some embodiments image processing step 1620 is a separate step, including where image processing is executed by separate devices.

Next, at step 1630, one or more image-based pre-delivery steps, discussed below, are performed based at least in part on the imaging/scan data 1615 from step 1610. As discussed in more detail below, step 1630 can include determining various parameters associated with the therapeutic treatment and (subsequent) imaging planning. In some embodiments, image-based pre-delivery steps (1630) may require more imaging (1610) before treatment delivery (1640). Step 1630 can include adapting a treatment plan based on the imaging data 1615 as part of an adaptive radiotherapy routine. In some embodiments, image-based pre-delivery steps 1630 may include real-time treatment planning. Embodiments may also include simultaneous, overlapping, and/or alternating activation of the imaging and therapeutic radiation sources, as described above. Real-time treatment planning may involve any or all of these types of imaging and therapeutic radiation activation techniques (simultaneous, overlapping, and/or alternating).

Next, at step 1640, therapeutic treatment delivery is performed using a source of high-energy radiation (e.g., MV radiation from therapeutic radiation source 20). Step 1640 delivers a treatment dose 1645 to the patient according to the treatment plan. In some embodiments, the IGRT method 1600 may include returning to step 1610 for additional imaging at various intervals (e.g., between fractions), followed by image-based pre-delivery steps (1630) and/or treatment delivery (1640) as required. In this manner the high-quality imaging data 1615 may be produced and utilized during IGRT using one apparatus 10 that is capable of adaptive therapy. As mentioned above, steps 1610, 1630, and/or 1640 may be executed simultaneously, overlapping, and/or alternating.

As mentioned above, IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly move the radiation source according to the treatment plan.

Figure 17:
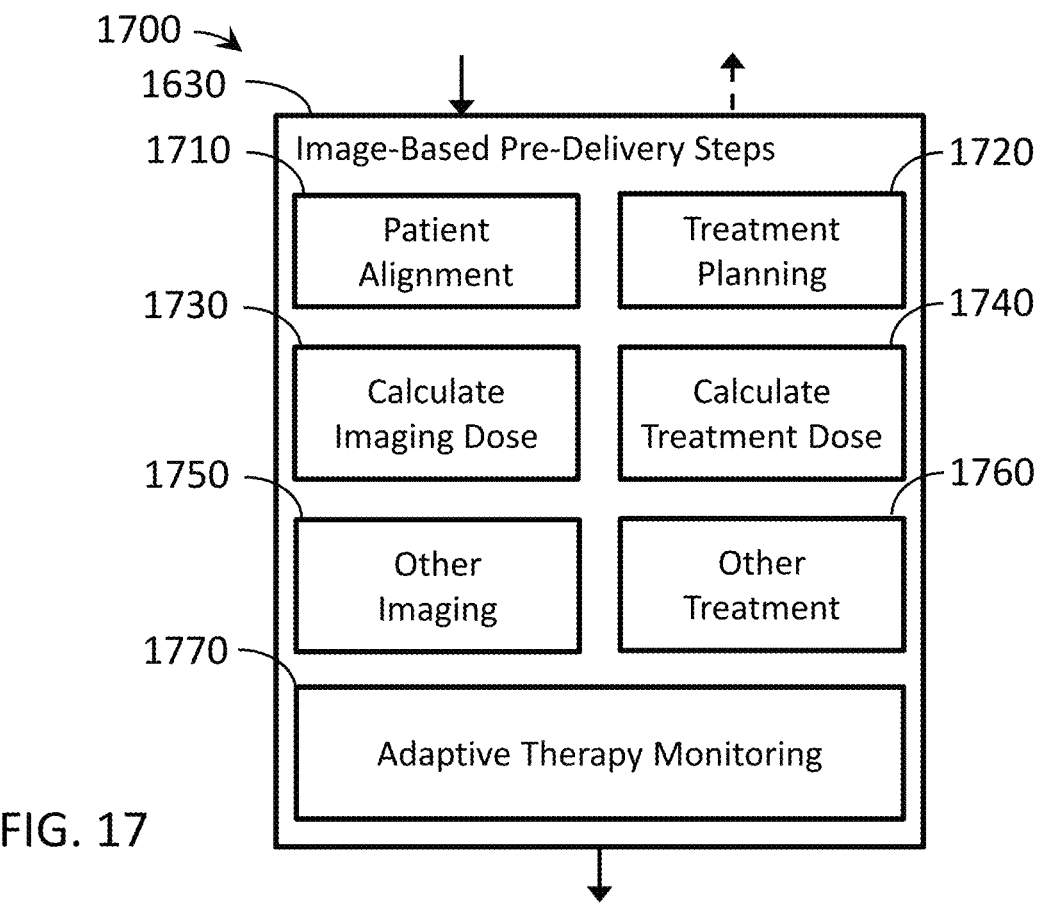
FIG. 17 is a block diagram depicting exemplary image-based pre-delivery steps/options.

FIG. 17 is a block diagram 1700 depicting exemplary image-based pre-delivery steps/options that may be associated with step 1630 above. It will be appreciated that the above-described multimodal apparatus 10 (e.g., as part of a radiotherapy device) can generate low energy and high energy images that can be used in a variety of ways, including for image-based pre-delivery steps (1630), without departing from the scope of the present invention. For example, images 1615 generated by the radiotherapy device can be used to setup or align a patient prior to treatment (1710). Patient alignment can include correlating or registering the current imaging data 1615 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information. An exemplary patient alignment process is described below.

Images generated by the multimodal apparatus 10 can also be used for treatment planning or re-planning (1720). In various embodiments, step 1720 can include confirming the treatment plan, modifying the treatment plan, generating a new treatment plan, and/or choosing a treatment plan from a set of treatment plans (sometimes referred to as "plan of the day"). For example, if the imaging data 1615 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 1615 (generated by the multimodal apparatus 10 at step 1610), the imaging data 1615 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the multimodal apparatus 10 can be used to calculate imaging dose (1730), which may be used for ongoing determinations of total dose to the patient and/or for subsequent imaging planning. The quality of subsequent imaging may also be determined as part of the treatment planning, for example, to balance quality and dosage. In accordance with another exemplary use case, images generated by the multimodal apparatus 10 can be used to calculate treatment dose (1740), which may be used for ongoing determinations of total dose to the patient and/or may be included as part of treatment planning or re-planning.

In accordance with other exemplary use cases, images generated by the multimodal apparatus 10 can be used in connection with planning or adjusting other imaging (1750) and/or other treatment (1760) parameters or plans, including, for example, as part of adaptive therapy and/or treatment plan generation. In accordance with another exemplary use case, images generated by the multimodal apparatus 10 can be used in connection with adaptive therapy monitoring (1770), which can include monitoring treatment delivery and adapting as required, including re-planning.

It should be appreciated that the image-based pre-delivery steps (1630) are not mutually exclusive. For example, in various embodiments, calculate treatment dose (1740) can be a step by itself and/or can be part of adaptive therapy monitoring (1770) and/or treatment planning (1720). In various embodiments, the image-based pre-delivery steps (1630) can be performed automatically and/or manually with human involvement.

Figure 18:
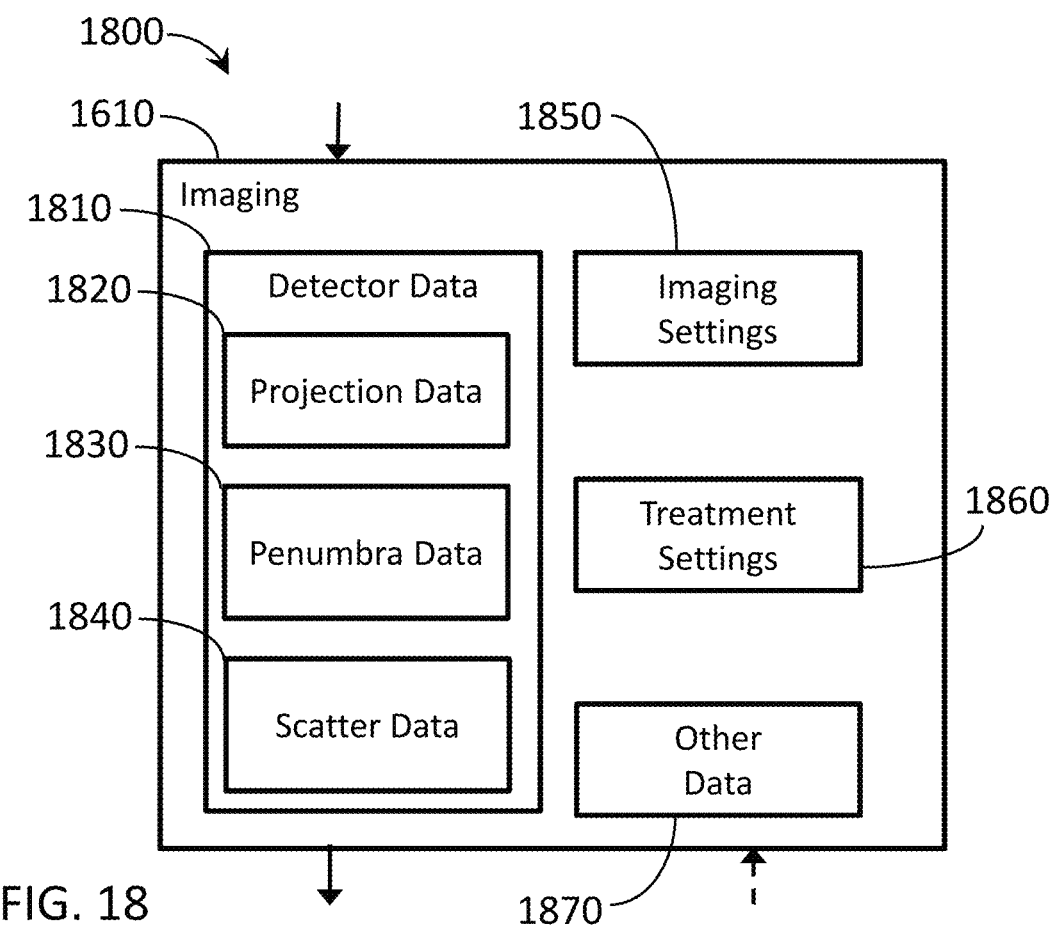
FIG. 18 is a block diagram depicting exemplary data sources that may be utilized during imaging and/or subsequent image-based pre-delivery steps.

FIG. 18 is a block diagram 1800 depicting exemplary data sources that may be utilized during imaging (1610) and/or subsequent image-based pre-delivery steps (1630). Detector data 1810 represents the data received by the radiation detectors 24, 34. The projection data 1820 is the data generated by the radiation incident in the collimated beam area, referred to above as the active region. The penumbra data 1830 is the data generated by the radiation incident in the penumbra area. The scatter data 1840 is the data generated by the radiation incident in the peripheral area outside of the penumbra area and/or the determined scatter as described above. In another embodiment, the scatter data 1840 can be used to determine the residual effect of the scatter from the therapeutic radiation source 20 (e.g., MV) when the two sources 20, 30 are operated simultaneously or in an interleaved manner.

In this manner, the penumbra data 1830 and/or the scatter data 1840 may be utilized to improve the quality of the images generated by the imaging step 1610. In some embodiments, the penumbra data 1830 and/or the scatter data 1840 may be combined with the projection data 1820 and/or analyzed in view of the applicable imaging settings 1850, treatment settings 1860 (e.g., if simultaneous imaging and/or treatment radiation), and any other data 1870 associated with the multimodal apparatus 10 at the time of the data collection at the detectors 24, 34. In other embodiments, the data may be used for the treatment planning step 1630.

Figure 19:
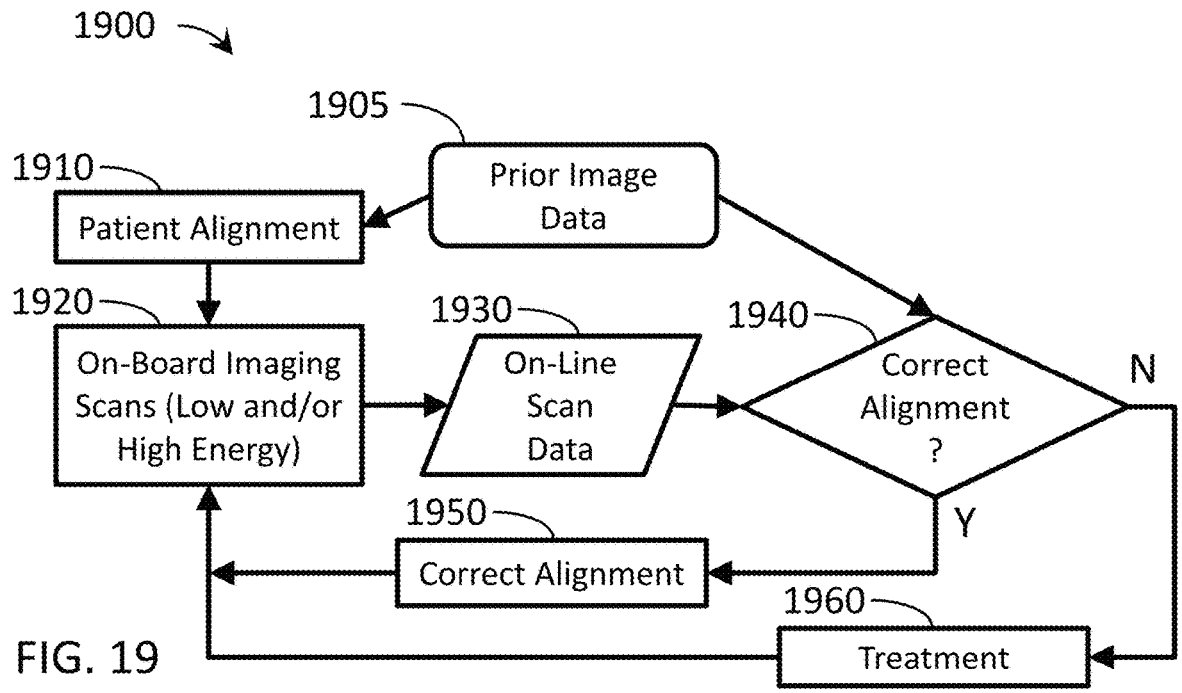
FIG. 19 is a flow chart depicting an exemplary method including patient setup or alignment using a radiotherapy device.
Figure 20:
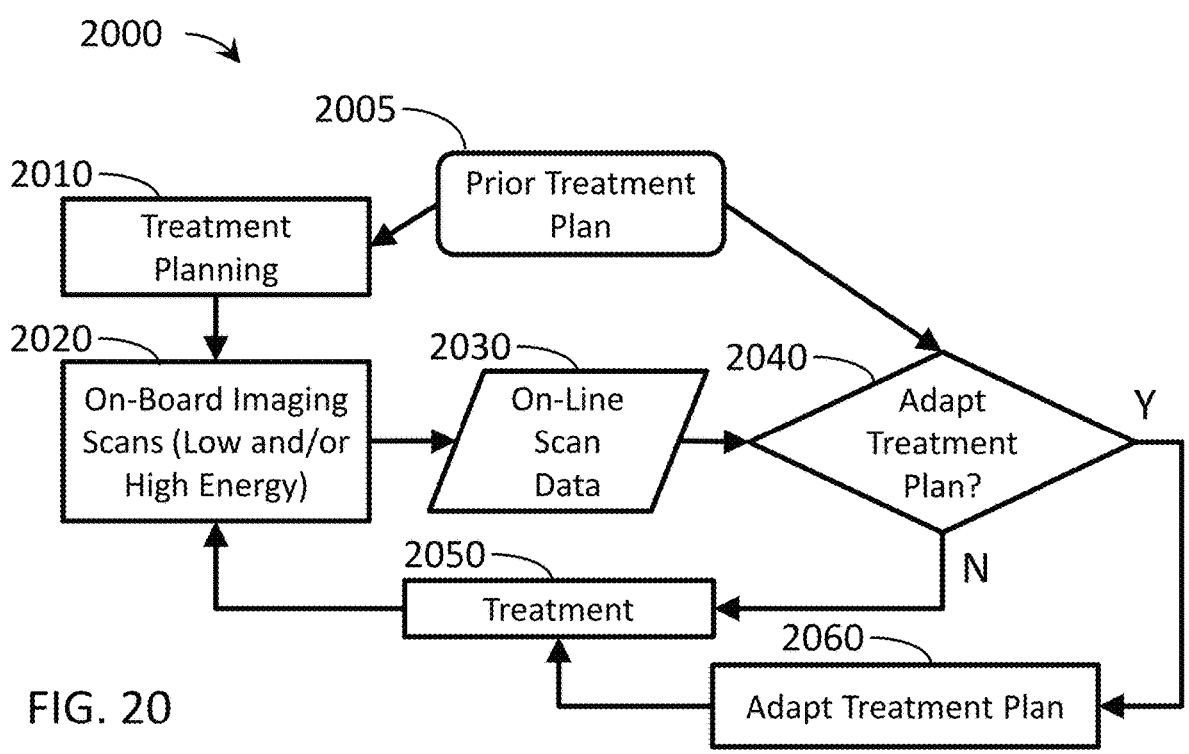
FIG. 20 is a flow chart depicting an exemplary method including adaptive IGRT using a radiotherapy device.

FIGS. 19 and 20 depict exemplary embodiments of imaging 1610, image-based pre-delivery steps 1630, and treatment delivery 1640 use cases, including examples of various forward and feedback sequences associated with on-board imaging using multimodal apparatus 10 during IGRT, including use of the methods described above.

FIG. 19 is a flow chart depicting an exemplary method 1900 including patient setup or alignment using a radiotherapy device (including, e.g., multimodal apparatus 10). Prior data 1905 can include images of the patient (e.g., a prior image, which may be a previously-acquired planning image, including a prior CT image, as discussed above). In some embodiments, the prior data 1905 is generated by the same radiotherapy device, but at an earlier time. At step 1910, an initial or preliminary alignment of the patient can be performed. Then, at step 1920, on-board imaging scans are performed using a low and/or high energy radiation source (e.g., kV radiation from source 30 and/or MV radiation from source 20) of multimodal apparatus 10, including, for example, as described in step 1610 above. In various embodiments, on-board imaging comprises a helical or circular scan with a fan or cone beam geometry. Step 1920 produces on-line imaging/scan data 1930 using the techniques described above. Imaging step 1920 can also include image processing to generate patient images based on the imaging/scan data 1930 (e.g., in accordance with methods described above), including, for example, as described in block 1620 above.

Next, step 1940 determines if an alignment correction is needed based at least in part on the on-line scan data 1930, including, for example, as described in block 1710 above. If an alignment correction or adjustment is needed, the method 1900 proceeds to step 1950 for an alignment correction, based at least in part on the on-line scan data 1930. Then, after the alignment correction, the method can return to step 1920 for additional imaging as a confirmation or further refinement loop. If an alignment correction or adjustment is not needed from step 1940, the method 1900 proceeds to step 1960 for treatment delivery. Then, after treatment, the method 1900 can return to step 1920 for additional imaging as a confirmation or further refinement loop.

FIG. 20 is a flow chart depicting an exemplary method 2000 including adaptive IGRT using a radiotherapy device (including, e.g., multimodal apparatus 10). Prior treatment plans 2005 can include treatment plans as well as images of the patient (e.g., a prior image, which may be a previously-acquired planning image, including a prior CT image, as discussed above), phantom information, models, a priori information, etc. In some embodiments, the prior data 2005 is generated by the same radiotherapy device, but at an earlier time. At step 2010, an initial or preliminary treatment plan can be adopted, for example, based on the prior treatment plan and any additional information. Then, at step 2020, on-board imaging scans are performed using a low and/or high energy radiation source (e.g., kV radiation from source 30 and/or MV radiation from source 20) of multimodal apparatus 10, including, for example, as described in step 1610 above. In various embodiments, on-board imaging comprises a helical or circular scan with a fan or cone beam geometry. Step 2020 produces on-line imaging/scan data 2030 using the techniques described above. Imaging step 2020 can also include image processing to generate patient images based on the imaging/scan data 2030 (e.g., in accordance with methods described above), including, for example, as described in block 1620 above.

Next, step 2040 determines if the treatment plan needs to be re-planned or adapted based at least in part on the on-line scan data 2030, including, for example, as described in block 1720 above. If a treatment plan does not need to be adapted or re-planned, the method 2000 proceeds to step 2050 for treatment delivery. If a treatment plan does need to be adapted or re-planned, the method 2000 proceeds to step 2060 for adapting the treatment plan, based at least in part on the on-line scan data 2030. Then, after adapting the treatment plan, the method can proceed to step 2050 for treatment delivery. Then, after treatment, the method 2000 can return to step 2020 for additional imaging as a confirmation or further refinement loop.

In some embodiments, methods 1900, 2000 and other methods can be executed simultaneously or in an interleaved manner based on a preferred workflow. For example, an on-board imaging scan can be performed and utilized as both the 1920 and 2020 scans to confirm treatment and continued alignment at the same time using the same data. In other embodiments, two or more of the image-based pre-delivery steps 1630 can be executed simultaneously or in an interleaved manner based on a preferred workflow, including where the same imaging data 1615 and/or image processing 1620 is utilized for more than one of the image-based pre-delivery steps 1630.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. A multimodal imaging apparatus, comprising:
a rotatable gantry system positioned at least partially around a patient support;
a first source of radiation coupled to the rotatable gantry system, the first source of radiation configured for imaging radiation;
a second source of radiation coupled to the rotatable gantry system, the second source of radiation configured for at least one of imaging radiation or therapeutic radiation, wherein the second source of radiation has an energy level more than the first source of radiation; and a first radiation detector coupled to the rotatable gantry system and positioned to receive radiation from at least one of the first source of radiation or the second source of radiation; and a processor configured to generate a first attenuation estimate wherein a first measured projection data from the first source of radiation comprises more attenuation than a second measured projection data from the second source of radiation, and the first attenuation estimate is associated with the first measured projection data and is based on the second measured projection data.

2. The apparatus of claim 1, wherein the first source of radiation comprises a kilo-electron volt peak photon energy (keV) up to 150 keV and the second source of radiation comprises a mega-electron volt peak photon energy (MeV) of 1 MeV or greater.

3. The apparatus of claim 1, wherein the second source of radiation comprises a peak energy of 3 MeV and an average energy of about 1 MeV.

4. The apparatus of claim 1, wherein the first measured projection data and the second measured projection data are acquired simultaneously or within about 50 ms of each other.

5. The apparatus of claim 1, wherein the second measured projection data comprises sparse projection data.

6. The apparatus of claim 1, wherein the first measured projection data or the second measured projection data are measured during a helical scan.

7. The apparatus of claim 1, wherein the first measured projection data or the second measured projection data are measured during a circular scan.

8. The apparatus of claim 1, further comprising at least one beamformer configured to adjust a shape of a radiation beam emitted by the first source of radiation or the second source of radiation.

9. The apparatus of claim 1, wherein at least one of the first source of radiation or the second source of radiation is configured to produce a fan beam shape.

10. The apparatus of claim 1, wherein at least one of the first source of radiation or the second source of radiation is configured to produce a cone beam shape.

11. The apparatus of claim 1, wherein the processor is configured to generate a reconstructed image based on the first attenuation estimate and the first measured projection data.

12. The apparatus of claim 1, wherein the first measured projection data comprises more scatter than the second measured projection data, and wherein a first scatter estimate associated with the first measured projection data is based on the second measured projection data.

13. The apparatus of claim 1, wherein the first measured projection data is measured at a first frequency, the second measured projection data is measured at a second frequency, the first frequency is less than the second frequency, and wherein interpolation of the first measured projection data is based on the second measured projection data.

14. The apparatus of claim 1, wherein the first measured projection data is measured at a first frequency, the second measured projection data is measured at a second frequency, the first frequency is less than the second frequency, and wherein a motion estimate of the first measured projection data is based on the second measured projection data.

15. The apparatus of claim 1, wherein the first source of radiation is coupled to a first rotatable gantry of the rotatable gantry system and the second source of radiation is coupled to a second rotatable gantry of the rotatable gantry system.

16. The apparatus of claim 1, further comprising a second radiation detector, wherein the first radiation detector is positioned to receive radiation from the first source of radiation and the second radiation detector is positioned to receive radiation from the second source of radiation.

17. The apparatus of claim 1, wherein the first measured projection data is integrated at a first time, the second measured projection data is integrated at a second time, the first time is longer than the second time, and wherein reconstruction of the first measured projection data is based on the second measured projection data.

18. The apparatus of claim 1, wherein the first measured projection data and the second measured projection data are acquired sequentially.

19. A treatment method, comprising:

receiving first measured projection data from a first source of radiation, the first source of radiation configured for imaging radiation;

receiving second measured projection data from a second source of radiation, the second source of radiation configured for at least one of imaging radiation or therapeutic radiation, wherein the second source of radiation has an energy level more than the first source of radiation, and wherein the first measured projection data comprises more attenuation than the second measured projection data;

determining a first attenuation estimate associated with the first measured projection data based on the second measured projection data; and reconstructing an image based on the first attenuation estimate and the first measured projection data.

20. The method of claim 19, wherein the first measured projection data and the second measured projection data are acquired simultaneously or within about 50 ms of each other.

21. The method of claim 19, further comprising registering a patient based on the reconstructed image during a patient registration workflow.

22. The method of claim 19, further comprising modifying a treatment plan based on the reconstructed image during an adaptive planning workflow.

23. The method of claim 19, further comprising calculating a treatment dose delivered to the patient based on the reconstructed image.

24. A radiotherapy delivery device comprising:

a rotatable gantry system positioned at least partially around a patient support;

a first source of radiation coupled to the rotatable gantry system, the first source of radiation being configured for imaging radiation;

a second source of radiation coupled to the rotatable gantry system, the second source of radiation being configured for at least one of imaging radiation or therapeutic radiation, wherein the second source of radiation has an energy level more than the first source of radiation; and a first radiation detector coupled to the rotatable gantry system and positioned to receive radiation from at least one of the first source of radiation or the second source of radiation;

wherein a first measured projection data from the first source of radiation comprises more attenuation than a second measured projection data from the second source of radiation, and wherein a first attenuation estimate associated with the first measured projection data is based on the second measured projection data; and a data processing system configured to:
  receive measured projection data from the first source of radiation and the second source of radiation, wherein a first measured projection data from the first source of radiation comprises more attenuation than a second measured projection data from the second source of radiation;
  determine a first attenuation estimate associated with the first measured projection data based on the second measured projection data; and
  combine the first measured projection data and the first attenuation estimate to reconstruct an image during IGRT.

* * * * *